(12) United States Patent
Chen et al.

(10) Patent No.: US 9,532,977 B2
(45) Date of Patent: Jan. 3, 2017

(54) CONTROLLED RELEASE ORAL DOSAGE FORMS OF POORLY SOLUBLE DRUGS AND USES THEREOF

(71) Applicant: Celgene Corporation, Summit, NJ (US)

(72) Inventors: Ming J. Chen, West Windsor, NJ (US); Ho-Wah Hui, Basking Ridge, NJ (US); Xiaole Shen, Livingston, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/938,714

(22) Filed: Nov. 11, 2015

(65) Prior Publication Data

US 2016/0128981 A1    May 12, 2016

Related U.S. Application Data

(63) Continuation-in-part of application No. 13/993,046, filed as application No. PCT/US2011/065151 on Dec. 15, 2011, now abandoned.

(60) Provisional application No. 61/424,003, filed on Dec. 16, 2010.

(51) Int. Cl.

| | |
|---|---|
| *A01N 37/18* | (2006.01) |
| *A61K 31/16* | (2006.01) |
| *A61K 31/4035* | (2006.01) |
| *A61K 9/00* | (2006.01) |
| *A61K 9/20* | (2006.01) |
| *A61K 31/00* | (2006.01) |

(52) U.S. Cl.
CPC ......... *A61K 31/4035* (2013.01); *A61K 9/0053* (2013.01); *A61K 9/0065* (2013.01); *A61K 9/205* (2013.01); *A61K 9/2009* (2013.01); *A61K 9/2027* (2013.01); *A61K 9/2054* (2013.01); *A61K 9/2086* (2013.01); *A61K 31/00* (2013.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,814,176 A | 3/1989 | Makino et al. |
| 4,915,952 A | 4/1990 | Ayer et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,451,409 A | 9/1995 | Rencher et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 5,945,125 A | 8/1999 | Kim |
| 6,210,710 B1 | 4/2001 | Skinner |
| 6,217,903 B1 | 4/2001 | Skinner |
| 6,251,430 B1 | 6/2001 | Zhang et al. |
| 6,635,280 B2 | 10/2003 | Shell et al. |
| 6,723,340 B2 | 4/2004 | Gusler et al. |
| 6,962,940 B2 | 11/2005 | Muller et al. |
| 8,263,128 B2 | 9/2012 | Curatolo et al. |
| 2003/0104053 A1 | 6/2003 | Gusler et al. |
| 2003/0104062 A1 | 6/2003 | Berner et al. |
| 2004/0254214 A1 | 12/2004 | Man et al. |
| 2008/0234359 A1 | 9/2008 | Muller et al. |
| 2008/0317863 A1 | 12/2008 | Nystrom et al. |
| 2010/0129445 A1 | 5/2010 | Asmussen et al. |
| 2010/0159001 A1 | 6/2010 | Cardinal et al. |
| 2010/0168475 A1 | 7/2010 | Saindane et al. |
| 2011/0160213 A1* | 6/2011 | Dhuppad ............. A61K 9/0056 514/248 |

FOREIGN PATENT DOCUMENTS

| | | | |
|---|---|---|---|
| DE | WO 2006097456 A1 * | 9/2006 | ........... A61K 9/0095 |
| EP | 0 941 071 B1 | 1/2004 | |
| WO | 97/22335 A1 | 6/1997 | |
| WO | 99/39698 A1 | 8/1999 | |
| WO | 2007/079182 A1 | 7/2007 | |
| WO | 2009/120167 A1 | 10/2009 | |
| WO | WO 2009120167 A1 * | 10/2009 | ......... A61K 31/4035 |

OTHER PUBLICATIONS

Carstensen, Drug Stability: Principles & Practices, Second Edition, Marcel Dekker, New York, NY, pp. 379-380 (1995).
List et al., "The myelodysplastic syndromes: biology and implications for management," J. Clin. Oncol., 8:1424-1441 (1990).
Man et al., "Discovery of (S)-N-[2-[1-(3-ethoxy-4-methoxyphenyl)-2-methanesulfonylethyl]1,3-dioxo-2,3-dihydro-1H-isoindol-4-yl] acetamide (apremilast), a potent and orally active phosphodiesterase 4 and tumor necrosis factor-alpha inhibitor," J. Med. Chem., 52:1522-1524 (2009).
Sakkinen et al., "Evaluation of microcrystalline chitosans for gastro-retentive drug delivery," Eur. J. Pharm. Sci., 19 (5):345-353 (2003).
The Merck Manual, 17th Edition, Merck & Company, West Point, PA, p. 953 (1999).
The United States Pharmacopeia, 23rd Edition, United States Pharmacopeial Convention, Inc., Rockville, MD, pp. 1843-1844 (1995).
Tierney et al. (eds), Current Medical Diagnosis & Treatmen 1998t, 37th Edition, Appleton & Lange, Stamford, CT, p. 793 (1998).
Wolff ed., Burger's Medicinal Chemistry and Drug Discovery, 5th Edition, John Wiley & Sons, Inc., pp. 172-178, 949-982 (1995).
Bonferoni et al., "Chitosan and its salts for mucosal and transmucosal delivery," Expert Opin. Drug Del., 6 (9):923-939 (2009).
Lee et al., "Bioadhesive-based dosage Proms: the next generation," J. Pharm. Sci., 89(7):850-866 (2000).

* cited by examiner

*Primary Examiner* — Jared D Barsky
(74) *Attorney, Agent, or Firm* — Jones Day

(57) ABSTRACT

Provided herein are controlled release oral dosage forms of poorly soluble drugs, methods of making the dosage forms, and methods of their use for the treatment of various diseases and/or disorders.

1 Claim, 23 Drawing Sheets

Gastroretentive tablet

Floating

Fast swelling

Bioadhesion

Blue circle = Observed
Red dot line = Predicted

The mean and confidence interval of both Formulation 98 and 101 in the Fed state fall within the 80-125% BE requirement of the 30 mg IR BID reference dose

CONTROLLED RELEASE ORAL DOSAGE FORMS OF POORLY SOLUBLE DRUGS AND USES THEREOF

The present application is a continuation-in-part of U.S. Nonprovisional patent application Ser. No. 13/993,046, filed Oct. 2, 2013, which is a national-stage filing under 35 U.S.C. §371 of International Application No. PCT/US2011/065151, filed Dec. 15, 2011, which claims priority to U.S. Provisional Patent Application No. 61/424,003, filed Dec. 16, 2010, the entirety of each of which is incorporated herein by reference.

1. FIELD OF INVENTION

Provided herein are controlled release oral dosage forms of poorly soluble drugs, methods of making the dosage forms, and methods of their use for the treatment of various diseases and/or disorders.

2. BACKGROUND OF THE INVENTION

One goal in developing a drug is to provide dosage forms which make it possible to maintain a certain amount or concentration of drug in a subject's body that will remain constant for several hours. Often this may not be achieved by traditional rapidly disintegrating tablets, as these tablets release the active ingredient contained therein all at once. For this reason, dosage forms have been developed which are capable of continuously releasing the drug contained therein in a controlled manner and over a prolonged period of time. Oral controlled drug delivery is typically by solid dosage forms including tablets, capsules, microspheres, granules and suspensions.

Gastroretentive systems, drug delivery systems having a prolonged retention time in the stomach, represent a promising approach to controlled release oral delivery of drugs. Many such systems have been developed. For example, U.S. Pat. Nos. 6,635,280 and 6,723,340 describe compositions for gastric retentive tablets which, upon oral administration, swell to a size such that the tablet cannot move out of the stomach easily. The drug is incorporated into a polymer matrix as the tablet swells and is released from the matrix into the gastric fluid by solution diffusion. See U.S. Pat. No. 6,635,280. Thus, the tablet acts as a controlled released gastroretentive system. Other similar gastroretentive systems are described in the art. See, e.g., European Patent No. EP 941071 B1.

A variety of polymeric excipients designed to expand or swell in the stomach have been used for the preparation of gastroretentive systems. See e.g., U.S. Pat. Nos. 6,210,710; 6,217,903; 5,945,125; 5,451,409; 4,915,952; U.S. Patent Publication Nos. 2003/0104053; 2003/0104062; and 2010/0129445. Such systems have been employed for the controlled release of poorly soluble drugs in particular. See, e.g., U.S. Pat. No. 6,635,280 and International Publication No. WO 97/22335. However, there exists a need for alternative controlled release dosage forms for drugs having poor aqueous solubility. Provided herein are controlled release dosage forms addressing this need.

3. SUMMARY OF THE INVENTION

Provided herein are controlled release oral dosage forms of poorly soluble drugs, methods of making the solid forms, and methods of their use for the treatment of various diseases and/or disorders.

The controlled release oral dosage forms provided herein comprise polymeric excipients which expand and/or become charged in the gastric fluid in acidic pH and control the release of the poorly soluble drug in the system.

Without being bound to a particular theory, the controlled release oral dosage forms provided herein are believed to enhance the bioavailability of a poorly soluble drug by increasing the time of release of the drug in the gastrointestinal tract. In some embodiments, the extended time of release of the poorly soluble drug occurs mainly in the stomach.

In some embodiments, the controlled release oral dosage forms provided herein comprise positively charged polymers, negatively charged polymers and swelling excipients, which when combined with a poorly soluble drug in particular weight ratios of ingredients provide controlled release of the poorly soluble drug. Without being bound to a particular theory, controlled release of the poorly soluble drug is achieved by action of the swelling excipients and the interaction of the polymers containing negative charges and positive charges in acidic pH of the stomach or upper gastrointestinal tract.

In one embodiment, the controlled release oral dosage form comprises one or more of each of the following: (i) a poorly soluble drug; (ii) a swelling excipient; (iii) a cationic polymer in acidic pH; and (iv) an anionic polymer in acidic pH. In some embodiments, the controlled release oral dosage form further comprises a water absorbing agent. In some embodiments, the controlled release oral dosage form further comprises one or more additional pharmaceutically acceptable excipients.

In one embodiment, the controlled release oral dosage form comprises one or more of each of the following: (i) a poorly soluble drug; (ii) a swelling excipient; (iii) a cationic polymer in acidic pH; (iv) an anionic polymer in acidic pH; and (v) a floating agent. In some embodiments, the controlled release oral dosage form further comprises a water absorbing agent. In some embodiments, the controlled release oral dosage form further comprises one or more additional pharmaceutically acceptable excipients.

In some embodiments, the poorly soluble drug is (S)—N-{2-[1-(3-ethoxy-4-methoxy-phenyl)-2-methanesulfonyl-ethyl]-1,3-dioxo-2,3-dihydro-1H-isoindol-4-yl}acetamide (Compound A).

In other embodiments, the poorly soluble drug is cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide (Compound B).

(S)—N-{2-[1-(3-ethoxy-4-methoxy-phenyl)-2-methanesulfonylethyl]-1,3-dioxo-2,3-dihydro-1H-isoindol-4-yl}acetamide (Compound A) has the following structure:

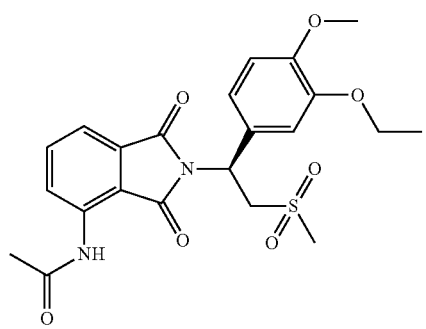 [SMILES: CCOc1cc([C@@H](CS(C)(=O)=O)N2C(=O)c3cccc(NC(C)=O)c3C2=O)ccc1OC]

Cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide (Compound B) has the following structure:

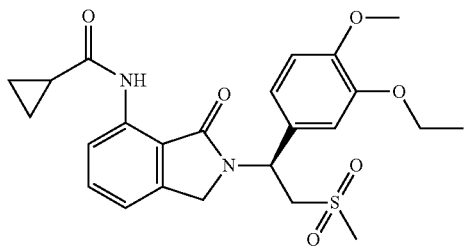 [SMILES: CCOc1cc([C@@H](CS(C)(=O)=O)N2Cc3cccc(NC(=O)C4CC4)c3C2=O)ccc1OC]

Provided herein are methods of treating, preventing or managing disorders ameliorated by the reduction of levels of TNF-α in a patient which comprises administering to a patient in need of such treatment, prevention or management a therapeutically or prophylactically effective amount of a compound provided herein, or a pharmaceutically acceptable prodrug, metabolite, polymorph, solvate, hydrate, or clathrate thereof.

DEFINITIONS

Figure 1:
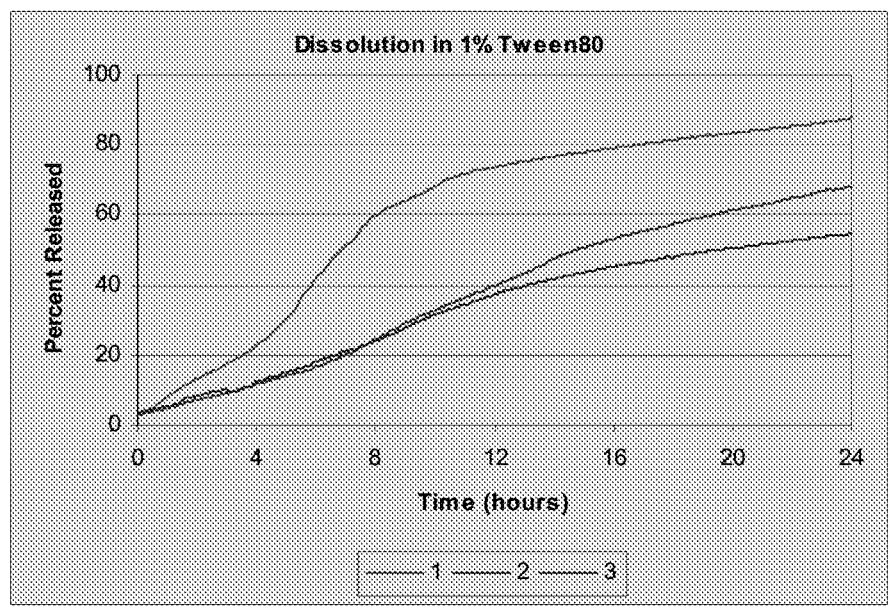
FIG. 1 shows the drug release profile of Compound A in Formulations 1 to 3 over 24 hours.

As used herein, the term "patient" refers to a mammal, particularly a human.

As used herein, the term "pharmaceutically acceptable salts" refer to salts prepared from pharmaceutically acceptable non-toxic acids or bases including inorganic acids and bases and organic acids and bases.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of a compound provided herein that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 Burger's Medicinal Chemistry and Drug Discovery, 172-178, 949-982 (Manfred E. Wolff ed., 5th ed. 1995).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise specified, "bioadhesive" is a property of a substance (i.e. a tablet) to adhere to biological surfaces such as, but not limited to, tissue and mucous.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein, term "adverse effects" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein and unless otherwise indicated, the phrases "reduce or avoid adverse effects" and "reducing or avoiding adverse effects" mean the reduction of the severity of one or more adverse effects as defined herein.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{rd}$ ed., 1843-1844 (1995).

As used herein and unless otherwise specified, the term "crystal forms," "crystalline forms" and related terms herein refer to solid forms that are crystalline. Crystal forms include single-component crystal forms and multiple-component crystal forms, and include, but are not limited to, polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "solvate" and "solvated," refer to a crystal form of a substance which contains solvent. The terms "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context and unless otherwise specified, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values.

As used herein and unless otherwise specified, a sample comprising a particular crystal form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the diluent, excipient or carrier must be compatible with the other ingredients of the formulation and not deleterious to the recipient thereof.

4. DETAILED DESCRIPTION

Because of the relatively poor absorption of Compound A in the colon, it is desirable to increase dissolution and residence time of Compound A in the stomach and small intestine.

In one embodiment, the increased dissolution and residence time of Compound A is achieved by a floating agent and a swelling agent that prolongs the residence time of Compound A in the upper GI tract.

In one embodiment, the increased dissolution and residence time of Compound A is achieved by the tablet's bioadhesive properties, whereby the tablet adheres to the membrane of the gastrointestinal tract, increasing the transit time in the small intestine. Examples of bioadhesive-based dosage forms can be found in Lee, *J. Pharm. Sci.* 2000, 89, 850.

Provided herein are controlled release oral dosage forms of poorly soluble drugs, methods of making the solid forms, and methods of their use for the treatment of various diseases and/or disorders.

The controlled release oral dosage forms provided herein comprise polymeric excipients which expand and/or become charged in the gastric fluid in acidic pH and control the release of the poorly soluble drug in the system.

Without being bound to a particular theory, the controlled release oral dosage forms provided herein are believed to enhance the bioavailability of a poorly soluble drug by increasing the time of release of the drug in the gastrointestinal tract. In some embodiments, the extended time of release of the poorly soluble drug occurs mainly in the stomach.

In certain embodiments, the release profile of the dosage forms provided herein achieve controlled release over an 8 to 24 hour period. In some embodiments, controlled release is achieved over about an 8 hour period; a 10 hour period; a 12 hour period; a 14 hour period; a 16 hour period; an 18 hour period; a 20 hour period; a 22 hour period; or a 24 hour period.

In some embodiments, the controlled release oral dosage forms provided herein comprise positively charged polymers, negatively charged polymers and swelling excipients, which when combined with a poorly soluble drug in particular weight ratios of ingredients provide controlled release of the poorly soluble drug. Without being bound to a particular theory, controlled release of the poorly soluble drug is achieved by action of the swelling excipients and the interaction of the polymers containing negative charges and positive charges in acidic pH of the stomach or upper gastrointestinal tract.

In one embodiment, the controlled release oral dosage form comprises one or more of each of the following: (i) a poorly soluble drug; (ii) a swelling excipient; (iii) a cationic polymer in acidic pH; and (iv) an anionic polymer in acidic pH. In some embodiments, the controlled release oral dosage form further comprises a water absorbing agent. In some embodiments, the controlled release oral dosage form further comprises one or more additional pharmaceutically acceptable excipients.

In one embodiment, provided herein is a controlled release oral dosage form comprising: (i) Compound A, or a pharmaceutically acceptable polymorph, solvate, or hydrate thereof; (ii) a swelling excipient; (iii) a cationic polymer in acidic pH; (iv) an anionic polymer in acidic pH; and (v) a floating agent. In certain specific embodiments, the floating agent is sodium bicarbonate. In some embodiments, the controlled release oral dosage form further comprises a water absorbing agent. In some embodiments, the controlled release oral dosage form further comprises one or more additional pharmaceutically acceptable excipients.

In one embodiment, a controlled release oral dosage form comprises:

(i) Compound A, or a pharmaceutically acceptable polymorph, solvate or hydrate thereof;

(ii) a swelling excipient in an amount from about 32.8% to about 50% by weight;

(iii) a cationic polymer in acidic pH;

(iv) an anionic polymer in acidic pH, and (v) sodium bicarbonate.

In one embodiment, Compound A is present in an amount of about 10%, about 20%, about 30%, about 40%, about 50%, about 60%, about 70%, about 80%, or about 90% by weight.

In a specific embodiment, Compound A is present in an amount of about 10% by weight.

In one embodiment, the swelling excipient is selected from the group consisting of polyethylene oxide, sodium carboxymethyl cellulose, hydroxypropyl cellulose, hydroxylpropyl methyl cellulose (HPMC), methyl celluloses, croscarmellose sodium, sodium starch glycolate, PolyplasdoneXL and Kollidon XL.

In a specific embodiment, the swelling excipient is sodium carboxymethyl cellulose.

In one embodiment, the swelling excipient is present in an amount of about 32.5% to about 37% by weight.

In a specific embodiment, the swelling excipient is present in an amount of about 34.5 percent.

In one embodiment, the cationic polymer in acidic pH is selected from the group consisting of chitosan, methacrylic acid-methyl methacrylate copolymer (in an about 1:1 ratio), methacrylic acid-methyl methacrylate copolymer (in an about 1:2 ratio), poly(butyl methacylate-co-2-dimethylaminoethyl methacrylate-co-methyl methacrylate) (in about an 1:2:1 ratio), and crosslinked acrylic acid copolymers.

In a specific embodiment, the cationic polymer in acidic pH is poly(butyl methacylate-co-2-dimethylaminoethyl methacrylate-co-methyl methacrylate) (in about an 1:2:1 ratio).

In one embodiment, the cationic polymer in acidic pH is present in an amount of about 5% to about 7% by weight.

In a specific embodiment, the cationic polymer in acidic pH is present in an amount of about 5 percent.

In one embodiment, the anionic polymer in acidic pH is selected from the group consisting of sodium alginate, sodium carboxymethyl cellulose (CMC), chondroitin sulfate, carrageenan, glycosaminoglycans, mucopolysaccharides, pectin, gelatin and hyalouronic acid.

In a specific embodiment, the anionic polymer in acidic pH is a sodium alginate.

In one embodiment, the anionic polymer in acidic pH is present in an amount of about 19% by weight.

In one embodiment, the sodium bicarbonate is in an amount of about 1%, about 2%, about 3%, about 4%, about 5%, about 6%, about 7%, about 8%, about 9%, about 10%, about 15%, about 20%, about 25%, about 30%, about 35%, about 40%, about 45%, or about 50% by weight.

In a specific embodiment, the sodium bicarbonate is in an amount of about 5% by weight.

In one embodiment, the controlled release oral dosage form further comprises a pH modifier.

In one embodiment, the pH modifier is citric acid.

In one embodiment, the pH modifier is present in an amount of about 6.5% to about 8% by weight.

In a specific embodiment, the cationic polymer in acidic pH is present in an amount of about 8 percent.

In one embodiment, the controlled release oral dosage form further comprises a disintegrant.

In one embodiment, the disintegrant is selected from the group consisting of lactose, microcrystalline cellulose, sodium starch glycolate, agar-agar, alginic acid, calcium carbonate, microcrystalline cellulose, croscarmellose sodium, crospovidone, polacrilin potassium, sodium starch glycolate, potato or tapioca starch, pre-gelatinized starch and mixtures thereof.

In a specific embodiment, the disintegrant is croscarmellose sodium.

In one embodiment, the disintegrant is present in an amount of about 5% by weight.

In one embodiment, the controlled release oral dosage form further comprises a lubricant.

In one embodiment, the lubricant is selected from the group consisting of a syloid silica gel, a coagulated aerosol of synthetic silica, a pyrogenic silicon dioxide, magnesium stearate, and mixtures thereof.

In a specific embodiment, the lubricant is magnesium stearate.

In one embodiment, the lubricant is present in an amount of about 5% by weight.

In one embodiment, the above-mentioned controlled release oral dosage form further comprises additional excipients, e.g., filler such as mannitol, and glydant such as colloidal silicon dioxide.

In one embodiment, about 5% to about 6% of Compound A is released after 1 hour, about 14% to about 15% of Compound A is released after 2 hours, about 35% to about 38% of Compound A is released after 4 hours, and about 55% to about 59% of Compound A is released after 6 hours, when dissolved in 2% Tween 80 in 50 mM sodium acetate buffer pH 4.5.

In a specific embodiment, about 5% of Compound A is released after 1 hour, about 14% of Compound A is released after 2 hours, about 36% of Compound A is released after 4 hours, and about 58% of Compound A is released after 6 hours, when dissolved in 2% Tween 80 in 50 mM sodium acetate buffer pH 4.5.

In one embodiment, about 71% to about 77% of the Compound A is released after 8 hours, about 86% to about 91% of the Compound A is released after 12 hours, and about 88% to about 94% of Compound A is released after 16 hours when dissolved in 2% Tween 80 in 50 mM sodium acetate buffer pH 4.5.

In a specific embodiment, about 75% of the Compound A is released after 8 hours, about 88% of the Compound A is released after 12 hours, and about 91% of Compound A is released after 16 hours when dissolved in 2% Tween 80 in 50 mM sodium acetate buffer pH 4.5.

In one embodiment, about 92% to about 98%% of the Compound A is released after 24 hours, when dissolved in 2% Tween 80 in 50 mM sodium acetate buffer pH 4.5. In a specific embodiment, about 95% of the Compound A is released after 24 hours, when dissolved in 2% Tween 80 in 50 mM sodium acetate buffer pH 4.5.

In a specific embodiment, when dissolved in 2% Tween 80 in 50 mM sodium acetate buffer pH 4.5, the percentage of Compound A released is about 5% after 1 hour, about 14% after 2 hours, about 36% after 4 hours, about 58 after 6 hours, about 75% after 8 hours, about 88% after 12 hours, and about 91% after 16 hours.

In a specific embodiment, a controlled release oral dosage form comprises:

(i) Compound A, or a pharmaceutically acceptable polymorph, solvate or hydrate thereof, in an amount of about 10% by weight;

(ii) sodium carboxymethyl cellulose in an amount of about 34.5% by weight;

(iii) poly(butyl methacylate-co-2-dimethylaminoethyl methacrylate-co-methyl methacrylate) (1:2:1) in an amount of about 5% by weight;

(iv) sodium alginate in an amount of about 19% by weight, and (v) sodium bicarbonate in an amount of about 5% by weight.

In another specific embodiment, the above controlled release oral dosage form further comprises (vi) citric acid in an amount of about 8% by weight; (vii) croscarmellose sodium in an amount of about 5% by weight; and (viii) magnesium stearate in an amount of about 1.5% by weight.

As provided herein, a "cationic polymer in acidic pH" or "positively charged polymer" refers to a polymer which is positively charged in acidic pH. "Acidic pH" refers to a pH<7. In some embodiments "acid pH" refers to a pH between 0 and 7; 0 and 5; 1 and 5; 0 and 4; 1 and 4; 0 and 3; or 1 and 3. Nonlimiting examples of cationic polymer in acidic pH include chitosan (e.g., Chitopharm® S and Chitoclear® 2832, 3504, 3548 and 3568), methacrylic acid-methyl methacrylate copolymer (1:1) (Eudragit® L100, Eudragit® L100-55), methacrylic acid-methyl methacrylate copolymer (1:2) (Eudragit® S 100), poly(butyl methacylate-co-2-dimethylaminoethyl methacrylate-co-methyl methacrylate) (1:2:1) (Eudragit® E PO), Eudragit® R LPO, Eudragit® R SPO, and crosslinked acrylic acid copolymers (Carbopol®).

As provided herein, an "anionic polymer in acidic pH" or "negatively charged polymer" refers to a polymer which is negatively charged in acidic pH. Nonlimiting examples of negatively charged polymers include sodium alginate (e.g., Protanal® LF 120M, Protanal® LF 200M, Protanal® LF 200D), sodium carboxymethyl cellulose (CMC), chondroitin sulfate, carrageenan (e.g., Gelcarin® 209, Gelcarin® 379), glycosaminoglycans, mucopolysaccharides, pectin, gelatin and hyalouronic acid.

As provided herein, a "swelling excipient" refers to an excipient which swells or grows in size when in contact with a liquid, e.g., an aqueous solution. Nonlimiting examples of swelling excipients include polymers, fibers and disintegrants, such as hydroxyethylcellulose (HEC, e.g., Natrosol® G, Natrosol® L), polyethylene oxide (e.g., Polyox® N10, Polyox® N12K, Polyox® N80, Polyox® N-205G, Polyox® N-1105 and Polyox® N750), sodium carboxymethyl cellulose (CMC, e.g., CMC 7L2P and CMC 7LF), hydroxypropyl cellulose, hydroxylpropyl methyl cellulose (HPMC), methyl celluloses, sodium crosscarmellose (Ac-Di-Sol®), sodium starch glycolate (Primojel®), Polyplasdone XL® and Kollidon® XL.

As provided herein, a "floating agent" refers to an excipient which facilitates the formulation's ability to float as a result of gas formation. A floating agent may alternatively be referred to as a "foaming agent" or an "effervescent agent." Nonlimiting examples of floating agents include sodium bicarbonate, sodium carbonate, potassium bicarbonate, potassium carbonate, calcium bicarbonate, and calcium carbonate.

Nonlimiting examples of water absorbing agent include humectants such as sorbitol, xylitol, maltitol, polymeric polyols, calcium chloride, sodium chloride, carrageenan (Gelcarin®), polyacrylic acid and hydrogel.

Fillers and processing aids may be used in the controlled release dosage forms provided herein. Examples of fillers include, but are not limited to, microcrystalline cellulose (e.g., MCC, Avicel PH102), lactose, dicalcium phosphate, pregelatinized starch and the mixture thereof.

Surfactants may be used in the controlled release dosage forms provided herein. Examples of surfactants include, but are not limited to, sodium laural sulfate (SLS) and ethylene oxide-propylene oxide block copolymers (e.g., Pluronic® F108).

As provided herein, "poorly soluble drug" refers to a drug which has limited solubility in aqueous media. Poorly soluble drugs are not readily absorbed through the gastrointestinal tract upon oral administration.

Examples of poorly soluble drugs provided herein include (S)—N-{2-[1-(3-ethoxy-4-methoxy-phenyl)-2-methanesulfonylethyl]-1,3-dioxo-2,3-dihydro-1H-isoindol-4-yl}acetamide (Compound A) and cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide (Compound B).

(S)—N-{2-[1-(3-ethoxy-4-methoxy-phenyl)-2-methanesulfonylethyl]-1,3-dioxo-2,3-dihydro-1H-isoindol-4-yl}acetamide (Compound A), described in Man et al. *J. Med. Chem.*, 2009, 52, 1522-1524, has the following structure:

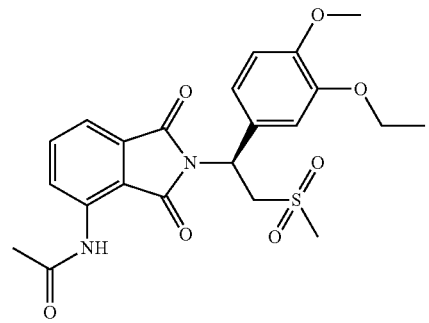 [SMILES: CCOc1cc([C@@H](CS(C)(=O)=O)N2C(=O)c3cccc(NC(C)=O)c3C2=O)ccc1OC]

Cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide (Compound B) has the following structure:

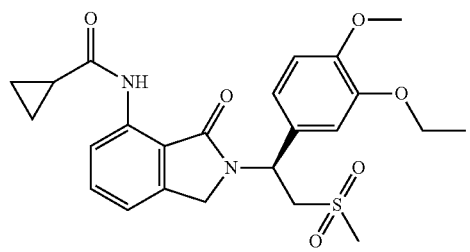 [SMILES: CCOc1cc([C@@H](CS(C)(=O)=O)N2Cc3cccc(NC(=O)C4CC4)c3C2=O)ccc1OC]

The aqueous room temperature solubilities of Compounds A and Compound B is 6.9 μg/mL and 2.0 μg/mL, respectively. Daily doses of Compound A ranging from 10 mg to 100 mg per day have been administered to approximately 1000 subject in clinical studies to date. At dose 10 mg/kg PO, the pharmacokinetic parameters of Compound A in monkeys indicated that the $t_{1/2}$ is about 2 hours. Therefore a controlled release dosage is clearly needed for Compound A.

In one embodiment, the poorly soluble drug provided herein is Compound A.

In one embodiment, Compound A is crystalline.

In one embodiment, Compound A is crystalline Form B.

In one embodiment, Compound A is amorphous.

In one embodiment, the controlled release oral dosage form comprises a poorly soluble drug, chitosan, an alginate, a swelling excipient, and optionally one or more additional excipients. In one embodiment, the swelling polymer is Natrosol. In one embodiment, the swelling polymer is Polyox.

In one embodiment, the chitosan has an average molecular weight of 10,000 to 5,000,000 Da. In another embodiment, the chitosan has an average molecular weight of 10,000 to 2,000,000 Da. In some embodiments, the chitosan has a degree of deacylation of at least 70%. In other embodiments, the chitosan has a degree of deacylation of at least 90%. In one embodiment, the particle size of the chitosan is such that it passes through 20 mesh screen.

In one embodiment, the alginate is a salt of alginic acid. In one embodiment, the alginate is sodium alginate.

In one embodiment, the controlled release oral dosage form comprises a poorly soluble drug, chitosan, a salt of carboxymethyl cellulose, a swelling excipient, and optionally one or more additional excipients.

In some embodiments, the swelling excipient is a polyethylene oxide or hydroxyethyl cellulose.

In some embodiments, the controlled release oral dosage form further comprises a disintegrant. In certain embodiments, the disintegrant is lactose. In other embodiments, the distintegrant is microcrystalline cellulose (MCC). In other embodiments, the disintegrant is sodium crosscarmellose. In other embodiments, the disintegrant is Primojel®.

Provided herein are methods of treating, preventing or managing disorders ameliorated by the reduction of levels of TNF-α in a patient which comprises administering to a patient in need of such treatment, prevention or management a therapeutically or prophylactically effective amount of a compound provided herein, or a pharmaceutically acceptable prodrug, metabolite, polymorph, solvate, hydrate, or clathrate thereof.

In particular embodiments, diseases or disorders ameliorated by the inhibition of TNF-α production in mammals include, but are not limited to: HIV; hepatitis; adult respiratory distress syndrome; bone resorption diseases; chronic obstructive pulmonary diseases; chronic pulmonary inflammatory diseases; asthma; dermatitis; cystic fibrosis; septic shock; sepsis; endotoxic shock; hemodynamic shock; sepsis syndrome; post ischemic reperfusion injury; meningitis; psoriasis; psoriatic arthritis; ankylosing spondylitis; Behcet's Disease; fibrotic disease; cachexia; graft rejection; auto immune disease; rheumatoid spondylitis; arthritic conditions, such as psoriatic arthritis, rheumatoid arthritis and osteoarthritis; osteoporosis; Crohn's disease; ulcerative colitis; inflammatory bowel disease; multiple sclerosis; systemic lupus erythematosus; cutaneous lupus erythematosus; pulmonary sarcoidosis; erythema nodosum leprosum (ENL) in leprosy; radiation damage; asthma; and hyperoxic alveolar injury. Such disorders further include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated by this method are multiple myeloma, malignant melanoma, malignant glioma, leukemia and solid tumors.

In some embodiments, provided herein are methods of treating or preventing cancer, including but not limited to, solid tumor, blood-borne tumor, leukemias, and in particular, multiple myeloma in a patient which comprises administering to a patient in need of such treatment or prevention a therapeutically effective amount of a compound provided herein, or a pharmaceutically acceptable prodrug, metabolite, polymorph, solvate, hydrate, or clathrate thereof; in particular wherein the patient is a mammal.

In another embodiment provided herein is a method of inhibiting PDE4 which comprises contacting PDE4 in a cell (e.g. a mammalian cell) with an effective amount of a compound provided herein, or a pharmaceutically acceptable prodrug, metabolite, polymorph, solvate, hydrate, or clathrate thereof (wherein particular embodiments encompass solid forms comprising Compound A as described herein).

In further embodiments, provided herein are methods of treating or preventing diseases or disorders ameliorated by the inhibition of PDE4 in a patient which comprises administering to a patient in need of such treatment or prevention a therapeutically or prophylactically effective amount of a compound provided herein, or a pharmaceutically acceptable prodrug, metabolite, polymorph, solvate, hydrate, or clathrate thereof. Disorders ameliorated by the inhibition of PDE4 include, but are not limited to, asthma, inflammation (e.g., inflammation due to reperfusion), chronic or acute obstructive pulmonary diseases, chronic or acute pulmonary inflammatory diseases, cutaneous lupus erythematosis, inflammatory bowel disease, Crohn's Disease, Behcet's Disease, or colitis.

In other embodiments, provided herein are methods of controlling cAMP levels in a cell which comprises contacting a cell with an effective amount of a compound provided herein, or a pharmaceutically acceptable prodrug, metabolite, polymorph, solvate, hydrate, or clathrate thereof. As used herein the term "controlling cAMP levels" includes preventing or reducing the rate of the breakdown of Adenosine 3',5'-cyclic monophosphate (cAMP) in a cell or increasing the amount of Adenosine 3',5'-cyclic monophosphate present in a cell, preferably a mammalian cell, more preferably a human cell. In a particular method, the rate of cAMP breakdown is reduced by about 10, 25, 50, 100, 200, or 500 percent as compared to the rate in comparable cells which have not been contacted with a compound of the invention.

In other embodiments, provided herein are methods of treating or preventing depression, asthma, inflammation, contact dermatitis, atopic dermatitis, psoriasis, psoriatic arthritis, rheumatoid arthritis, osteoarthritis, cutaneous lupus erythematosis, ankylosing spondylitis, inflammatory skin disease, inflammation due to reperfusion, chronic or acute obstructive pulmonary diseases, chronic or pulmonary inflammatory diseases, autoimmune diseases, inflammatory bowel disease, Crohn's Disease, Behcet's Disease or colitis in a patient which comprises administering to a patient in need of such treatment or prevention a therapeutically or prophylactically effective amount of a compound provided herein, or a pharmaceutically acceptable prodrug, metabolite, polymorph, solvate, hydrate, or clathrate thereof; in particular wherein the patient is a mammal.

In other embodiments, provided herein are methods of treating or preventing myelodysplastic syndrome (MDS) which comprises administering to a patient in need of such treatment or prevention a therapeutically or prophylactically effective amount of a compound provided herein, or a pharmaceutically acceptable solvate, hydrate, clathrate, or prodrug thereof. MDS refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. See *The Merck Manual* 953 (17th ed. 1999) and List et al., 1990, *J. Clin. Oncol.* 8:1424.

Also provided herein are methods of treating or preventing myeloproliferative disease (MPD) which comprises administering to a patient in need of such treatment or prevention a therapeutically or prophylactically effective amount of a compound provided herein, or a pharmaceutically acceptable solvate, hydrate, clathrate, or prodrug thereof. Myeloproliferative disease (MPD) refers to a group of disorders characterized by clonal abnormalities of the hematopoietic stem cell. See e.g., *Current Medical Diagnosis & Treatment*, pp. 499 (37th ed., Tierney et al., ed., Appleton & Lange, 1998).

Also provided herein are methods of treating, preventing or managing pain, including, but not limited to, complex regional pain syndrome, which comprises administering to a patient in need of such treatment, prevention or management a therapeutically or prophylactically effective amount of a compound provided herein, or a pharmaceutically acceptable solvate, hydrate, clathrate, or prodrug thereof. In a specific embodiment, the administration is before, during or after surgery or physical therapy directed at reducing or avoiding a symptom of complex regional pain syndrome in the patient.

In some methods herein, a compound provided herein, or a pharmaceutically acceptable polymorph, prodrug, solvate, hydrate, or clathrate thereof, is adjunctively administered with at least one additional therapeutic agent. Examples of additional therapeutic agents include, but are not limited to, anti-cancer drugs, anti-inflammatories, antihistamines and decongestants.

Controlled Release Oral Dosage Forms

The controlled release dosage forms provided herein comprise positively charged polymers, negatively charged polymers and swelling excipients, which when combined with a poorly soluble drug in particular weight ratios of ingredients provide controlled release of the poorly soluble drug. Without being bound to a particular theory, controlled release of the poorly soluble drug is achieved by action of the swelling excipients and the interaction of the polymers containing negative charges and positive charges in acidic pH of the stomach or upper gastrointestinal tract.

In certain embodiments, the release profile of the dosage forms provided herein achieves controlled release over an 8 to 24 hour period.

The controlled release dosage forms provided herein use opposite charged polymeric excipients to form an inter-penetrating network in situ when the compositions contact water, gradually forming a gel system in the outer shell of the dosage form (e.g., tablet). A water absorbing agent enhances the rate of water penetration to boost the swelling of the inter-penetrating system in a short time. Furthermore, specific excipients which contribute to the swelling result in a synergistic swelling ratio with the charged inter-penetrating network system.

Controlled release oral dosage forms provided herein comprise one or more of each of the following: (i) a poorly soluble drug; (ii) a swelling excipient; (iii) a cationic polymer in acidic pH; and (iv) an anionic polymer in acidic pH. In some embodiments, the controlled release oral dosage form further comprises a water absorbing agent. In some embodiments, the controlled release oral dosage form further comprises one or more additional pharmaceutically acceptable excipients.

Only certain pH-sensitive polymers combined with swelling excipients can achieve a beneficial gastroretentive systems provided herein. In the controlled release dosage forms provided herein, specific polymers are selected which bear positive and negative charges at the pH of the stomach, and with specific swelling ingredients, the systems show the gastroretentive effects by swelling the matrix for extended controlled release of a drug or drugs. Further, in some embodiments, the rates of release of drugs from the system may be controlled by altering the ratio of ingredients, e.g., of charged polymers and swelling excipients. The ranges of molecular weight of polymers in the inter-penetrating system also may contribute to the controlled release pattern of the drugs.

Chitosans are exemplary positively charged polymers that may be used in the oral dosage forms provided herein. Chitosans have been described in the literature as pharmaceutical ingredients for controlled release systems. See e.g., *Eur J Pharm Sci.*, 2003, 19(5):345-53. However, the use of chitosans is limited to controlled release systems for drug delivery in the colon, not the gastroretentive system. The gastric retention time described in these systems is too short; drugs pass the absorption window in stomach before being released.

As provided herein, the molecular weight, particle size, and degree of deacetylation of chitosans are factors which may affect release rates and lengthen the widow of absorption of a drug. In some embodiments, the degree of deacetylation of chitosans used in the formulations herein is greater than 90%. In the prior art, chitosan was prepared by dissolving the granules in acid solution first, followed by drying to lumps and homogenized. As provided herein, chitosan granules are used directly without re-processing.

The controlled release dosage forms provided herein are developed such that the amount of the total excipients required for swelling and retaining in the stomach over time is determined such that the system delivers the drug in a controlled release manner. Certain combinations of positively charged polymer (e.g., chitosan), negatively charged polymer (e.g. sodium alginate) and swelling ingredients (e.g., Ac-Di-Sol® or Natrosol®) are proved to be a synergistic controlled release system. Such compositions result in extended controlled release profiles by USP I in vitro dissolution method using Distek dissolution apparatus. See Examples 4-6.

Pharmaceutical Compositions

Pharmaceutical compositions and dosage forms provided herein typically also comprise one or more pharmaceutically acceptable excipient, diluent or carrier.

In some embodiments, a pharmaceutical composition provided herein comprises one or more solid forms a compound provided herein and at least one additional therapeutic agent. Examples of additional therapeutic agents include, but are not limited to: anti-cancer drugs and anti-inflammation therapies including, but not limited to, those provided herein.

Examples of oral dosage forms include, but are not limited to: tablets; caplets; capsules, such as soft elastic gelatin capsules; cachets; troches; lozenges; dispersions; aerosols (e.g., inhalers); gels; liquid dosage forms suitable for oral administration to a patient, including suspensions (e.g., aqueous or non-aqueous liquid suspensions, oil-in-water emulsions, or a water-in-oil liquid emulsions), solutions, and elixirs.

The composition, shape, and type of dosage forms provided herein will typically vary depending on their use. These variations will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Lactose-free compositions of the invention can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The dosage forms provided herein may further comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein lie within the range of from about 1 mg to about 1,000 mg per day, given as a single once-a-day dose in the morning but preferably as divided doses throughout the day. More specifically, the daily dose is administered twice daily in equally divided doses. Specifically, a daily dose range may be from about 5 mg to about 500 mg per day, more specifically, between about 10 mg and about 200 mg per day. In managing the patient, the therapy may be initiated at a lower dose, perhaps about 1 mg to about 25 mg, and increased if necessary up to about 200 mg to about 1,000 mg per day as either a single dose or divided doses, depending on the patient's global response.

The oral dosage forms provided herein may be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally *Remington's Pharmaceutical Sciences,* 18th ed., Mack Publishing, Easton Pa. (1990).

Typical oral dosage forms provided herein are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

In certain embodiments, the dosage form provided herein is a 5 mg, 10 mg, 15 mg, 20 mg, 25 mg, 30 mg, 40 mg, 50 mg, 60 mg, 75 mg, 100 mg, 150 mg, 200 mg, 250 mg, 300 mg, 400 mg, 500 mg, 750 mg or 1000 mg tablet.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101™, AVICEL-PH-103™, AVICEL RC-581™, AVICEL-PH-105™ (available from FMC Corporation, American Viscose Division, Avicel Sales, Marcus Hook, Pa.), and mixtures thereof. A specific binder is a mixture of microcrystalline cellulose and sodium carboxymethyl cellulose (sodium CMC) sold, for example, as AVICEL RC-581™. Suitable anhydrous or low moisture excipients or additives include AVICEL-PH-103™ and Starch 1500 LM™.

Disintegrants may be used in the compositions herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that may be used herein include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that may be used herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200™, manufactured by W.R. Grace Co. of Baltimore, Md.), a coagulated aerosol of synthetic silica (marketed by Degussa Co. of Plano, Tex.), CAB-O-SIL™ (a pyrogenic silicon dioxide product sold by Cabot Co. of Boston, Mass.), and mixtures thereof. If used at all, lubricants are typically used in an amount of less than about one weight percent of the pharmaceutical compositions or dosage forms into which they are incorporated.

Dosage forms comprising a compound may be administered by controlled release means or by delivery devices that are well known to those of ordinary skill in the art. Examples include, but are not limited to, those described in U.S. Pat. Nos. 3,536,809; 3,598,123; 3,845,770; 3,916,899; 4,008,719; 5,059,595; 5,073,543; 5,120,548; 5,354,556; 5,591,767; 5,639,476; 5,674,533 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

The above referenced U.S. Pat. Nos. 3,598,123, 5,639,476, and 5,354,556 disclose the use of sodium bicarbonate in pharmaceutical formulations. U.S. Pat. No. 3,598,123, for example, discloses the use of sodium bicarbonate as a foaming agent.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Methods of Treatment

The invention encompasses methods of treating, preventing and managing diseases or disorders ameliorated by the reduction of levels of TNF-α in a patient which comprise administering to a patient in need of such treatment, prevention or management a therapeutically or prophylactically effective amount of a controlled release oral dosage form provided herein.

Disorders ameliorated by the inhibition of TNF-α include, but are not limited to: heart disease, such as congestive heart failure, cardiomyopathy, pulmonary edema, endotoxin-mediated septic shock, acute viral myocarditis, cardiac allograft rejection, and myocardial infarction; depression, asthma, inflammation, contact dermatitis, atopic dermatitis, psoriasis, psoriatic arthritis, rheumatoid arthritis, osteoarthritis, cutaneous lupus erythematosis, ankylosing spondylitis, inflammatory skin disease, inflammation due to reperfusion, chronic or acute obstructive pulmonary diseases, chronic or pulmonary inflammatory diseases, autoimmune diseases, inflammatory bowel disease, Crohn's Disease, Behcet's Disease or colitis; solid tumors, including but not limited to, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma; and blood-borne tumors including but not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute non-lymphocyctic leukemia, acute undifferentiated leukemia, chronic myelocytic leukemia "CML", chronic lymphocytic leukemia "CLL", hairy cell leukemia, multiple myeloma and acute and chronic leukemias, for example, lymphoblastic, myelogenous, lymphocytic, and myelocytic leukemias.

Specific methods provided herein further comprise the administration of an additional therapeutic agent. Examples of additional therapeutic agents include, but are not limited to, anti-cancer drugs such as, but are not limited to: alkylating agents, nitrogen mustards, ethylenimines, methylmelamines, alkyl sulfonates, nitrosoureas, triazenes, folic acid analogs, pyrimidine analogs, purine analogs, vinca alkaloids, epipodophyllotoxins, antibiotics, topoisomerase inhibitors and anti-cancer vaccines.

Specific additional therapeutic agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Embodiments herein further encompass a method of treating or preventing diseases or disorders ameliorated by the inhibition of TNF-α in a patient. Such diseases and disorders include, but are not limited to: heart disease, such as congestive heart failure, cardiomyopathy, pulmonary edema, endotoxin-mediated septic shock, acute viral myocarditis, cardiac allograft rejection, and myocardial infarction; depression, asthma, inflammation (e.g., contact dermatitis, atopic dermatitis, psoriasis, psoriatic arthritis, rheumatoid arthritis, osteoarthritis, cutaneous lupus erythematosis, ankylosing spondylitis, inflammatory skin disease, inflammation due to reperfusion), chronic or acute obstructive pulmonary diseases, chronic or pulmonary inflammatory diseases, autoimmune diseases, inflammatory bowel disease, Crohn's Disease, Behcet's Disease or colitis. In a one embodiment, the disease or disorder to be treated or prevented is chronic obstructive pulmonary disease.

Specific methods provided herein may comprise the administration of an additional therapeutic agent such as, but not limited to, anti-inflammatory drugs, antihistamines and decongestants. Examples of such additional therapeutic agents include, but are not limited to: antihistamines including, but not limited to, ethanolamines, ethylenediamines, piperazines, and phenothiazines; antinflammatory drugs; NSAIDS, including, but not limited to, aspirin, salicylates, acetominophen, indomethacin, sulindac, etodolac, fenamates, tolmetin, ketorolac, diclofenac, ibuprofen, naproxen, fenoprofen, ketoprofen, flurbiprofen, oxaprozin, piroxicam, meloxicam, pyrazolon derivatives; and steroids including, but not limited to, cortical steroids and adrenocortical steroids.

As stated above, the dosage forms provided herein may be used in the treatment or prevention of a wide range of diseases and conditions. The magnitude of a prophylactic or therapeutic dose of a particular active ingredient of the invention in the acute or chronic management of a disease or condition may vary with the nature and severity of the disease or condition and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1,000 mg per day, given as a single once-a-day dose preferably as divided doses throughout a day. More specifically, the daily dose is administered twice daily in equally divided doses. Specifically, a daily dose range may be from about 5 mg to about 500 mg per day, more specifically, between about 10 mg and about 200 mg per day. Specifically, the daily dose may be administered in 5 mg, 10 mg, 15 mg, 20 mg, 25 mg, 30 mg, 50 mg, or 100 mg dosage forms (Q.D. or B.I.D.). In managing the patient, the therapy should be initiated at a lower dose, perhaps about 1 mg to about 25 mg, and increased if necessary up to about 200 mg to about 1,000 mg per day as either a single dose or divided doses, depending on the patient's global response. Alternatively, the daily dose is from 0.01 mg/kg to 100 mg/kg.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Kits

This invention encompasses kits which, when used by the medical practitioner, can simplify the administration of appropriate amounts of active ingredients to a patient.

A typical kit of the invention comprises a unit dosage form of a compound provided herein, or a pharmaceutically acceptable solid form or prodrug thereof, and a unit dosage form of a second active ingredient. Examples of second active ingredients include, but are not limited to, those listed herein.

Kits of the invention can further comprise devices that are used to administer the active ingredient(s). Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples. The present application incorporates by reference the entirety of U.S. Pat. No. 6,962,940, including the Examples provided therein.

Example 1

SYNTHESIS OF 2-[1-(3-ETHOXY-4-METHOXY-PHENYL)-2-METHYLSULFONYLETHYL]-4-ACETYLAMINOISOINDOLINE-1,3-DIONE

A stirred solution of 1-(3-ethoxy-4-methoxyphenyl)-2-methyl sulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ: 1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CH), 3.85 (s, 3H, CH3), 4.11 (q, J=7 Hz, 2H, CH$_2$), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) δ: 14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for $C_{22}H_{24}NO_7S$: C, 57.38; H, 5.25; N, 6.08. Found: C, 57.31; H, 5.34; N, 5.83.

Example 2

SYNTHESIS OF (+)2-[1-(3-ETHOXY-4-METHOXYPHENYL)-2-METHYLSULFONYL-ETHYL]-4-ACETYLAMINOISOINDOLINE-1,3-DIONE

Preparation of 3-aminopthalic acid

10% Pd/C (2.5 g), 3-nitrophthalic acid (75.0 g, 355 mmol) and ethanol (1.5 L) were charged to a 2.5 L Parr hydrogenator under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) δ: 3.17 (s, 2H), 6.67 (d, 1H), 6.82 (d, 1H), 7.17 (t, 1H), 8-10 (br, s, 2H); $^{13}$C-NMR (DMSO-d6) δ: 112.00, 115.32, 118.20, 131.28, 135.86, 148.82, 169.15, 170.09.

Preparation of 3-acetamidophthalic anhydride

A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to about 25° C. and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

Resolution of 2-(3-ethoxy-4-methoxyphenyl-1-(methylsulphonyl)-eth-2-ylamine

A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$ @ pH 7.0, Ultron Chiral ES-OVS from Agilent Technologies, 150 mm×4.6 mm, 0.5 mL/min., @ 240 nm): 18.4 min (S-isomer, 99.2%), 25.5 min (R-isomer, 0.8%).

Preparation of Compound A

A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g, 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of S-{2-[1-(3-ethoxy-4-methoxyphenyl)-2-methylsulfonylethyl]-4-acetamidoisoindoline-1,3-dione} with 98% ee. Chiral HPLC (15/85 EtOH/20 mM KH$_2$PO$_4$ @ pH 5, Ultron Chiral ES-OVS from Agilent Technology, 150 mm×4.6 mm, 0.4 mL/min, @ 240 nm): 25.4 min (S-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H); $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

Specific polymorphic solid forms of Compound A may be used in the dosage forms provided herein, as described in U.S. Patent Publication No. 2008/0234359.

Example 3

SYNTHESIS OF CYCLOPROPANECARBOXYLIC ACID {2-[(1S)-1-(3-ETHOXY-4-METHOXY-PHENYL)-2-METHANE-SULFONYL-ETHYL]-3-OXO-2,3-DIHYDRO-1H-ISOINDOL-4-YL}-AMIDE

Preparation of methyl 2-methyl-6-nitrobenzoate

A mixture of 2-methyl-6-nitrobenzoic acid (300.0 g, 1.66 moles, from Acros Organics, Morris Plains, N.J.) and trimethyl orthoacetate (298.3 g, 2.48 moles, from Aldrich Chemicals, Milwaukee, Wis.) was charged into a 3-L 3-necked flask at about 20-25° C. under nitrogen. The reaction mixture was gradually heated and the low-boiling point components generated during the reaction were distilled off to an internal temperature of 95-100° C. After 2 hours, the reaction mixture was cooled to 20-25° C. over 1-2 hours. After heptane (1.50 L, from Aldrich Chemicals) was charged into the reaction mixture over 1.0-1.5 hours, the reaction mixture was seeded with methyl 2-methyl-6-nitrobenzoate (0.5 g) when it became turbid. The suspension was cooled to 0-5° C. over 0.5-1 hour and kept at 0-5° C. for another 1.5-2 hours. The solid was collected by filtration under vacuum, washed with heptane (3×300 mL), and dried to a constant weight in a tray at 30-35° C. under a vacuum at 100-120 torr. The yield of methyl 2-methyl-6-nitrobenzoate was 292.0 g (91%), based on 300.0 g of 2-methyl-6-nitrobenzoic acid. The product was found to have a purity of >99% measured by HPLC based on area percentage, and a water content of <0.1% measured by Karl Fisher titration.

Preparation of methyl 2-bromomethyl-6-nitrobenzoate

A mixture of methyl 2-methyl-6-nitrobenzoate (200.0 g, 1.02 moles, previously prepared), 1,3-dibromo-5,5-dimethylhydantoin (DBH, 162.0 g, 0.57 mole, from Aldrich Chemicals) and methyl acetate (1.20 L, from Aldrich Chemicals) was charged into a 3-L three-necked flask at about 20-25° C. under nitrogen. After the reaction mixture was refluxed for 0.5-1 hour, a solution of 2,2'-azobisisobutyronitrile (AIBN, 8.6 g, 52 mmol, from Aldrich Chemicals) in 100 mL of methyl acetate was charged over 15-30 minutes. The reaction mixture was refluxed for 6.5-8 hours until the amount of unreacted 2-methyl-6-nitrobenzoate was less than 5-10%. The reaction mixture was cooled to 15-18° C. and kept at 15-18° C. for 50-60 minutes. The solid was filtered, washed with cold (i.e., 5-10° C.) methyl acetate (2×100 mL) until there was less than 3% of methyl 2-bromomethyl-6-nitrobenzoate remained in the solid. Next, after heptane (1.00 L) was charged into the filtrate, the upper layer organic phase was washed with 2% of brine (2×500 mL) and deionized water (1-2×500 mL) until there was less than 0.5% (area percentage at 210 nm) of unreacted 5,5-dimethylhydantoin according to measurement by HPLC. After the solution was concentrated under a reduced pressure to remove about 1.80-1.90 L of methyl acetate, methyl tert-butyl ether (MTBE, 300 mL) was charged. After the reaction mixture was refluxed at 65-70° C. for 10-15 minutes, the solution was cooled to 50-55° C. over 0.5-1 hour and seeded with 500 mg of methyl 2-bromomethyl-6-nitrobenzoate at 45-50° C. The suspension was cooled to 20-25° C. and kept at 20-25° C. for 2-3 hours. The solids were collected by filtration, washed with 5-10° C. a cold mixture of heptane and MTBE in a volume ratio of 1:2 (2×100 mL), and dried to a constant weight at 20-25° C. under a vacuum at 100-120 torr. The yield of methyl 2-bromomethyl-6-nitrobenzoate was 185.2 g (66%), based on 200.0 g input of methyl 2-methyl-6-nitrobenzoate. The product was found to have a purity of >98% measured by HPLC based on area percentage, and a water content of <0.1% measured by Karl Fisher titration.

Preparation of (1S)-1-(3-ethoxy-4-methoxyphenyl)-2-methanesulfonyl-ethylamine

After a mixture of (1S)-1-(3-ethoxy-4-methoxyphenyl)-2-methanesulfonyl-ethylamine N-acetyl-L-Leucine salt (1.10 kg, 2.46 moles), deionized water (4.40 L), and dichloromethane (DCM, 5.50 L) was charged into a reaction vessel, a solution of sodium hydroxide (196.0 g, 4.90 moles) in 1.00 L of deionized water was charged into the reaction vessel over about 5 minutes at 15-25° C. The resulting mixture was stirred for at least 10 minutes at 15-25° C. and then the aqueous and organic phases were allowed to separate. The pH of the upper aqueous phase was maintained or adjusted at pH 13-14. The phases were separated and the upper aqueous phase was extracted with DCM (2×4.4 L). The pH of the aqueous phase was maintained at 13-14 throughout the extractions. The DCM extracts were combined and washed with deionized water (3.3 L) until the pH of the aqueous phase reached 11 or less. DCM was removed under vacuum below 35° C. The water content of the residual solid should be <0.1% w/w as measured by Karl Fisher titration. The residual solid was dried azeotropically with more DCM. The solid was dried to a constant weight in vacuo at 30-35° C. to give (1S)-1-(3-ethoxy-4-methoxyphenyl)-2-methanesulfonyl-ethylamine as a white powder (639.0-672.0 g, 95-100% yield).

Preparation of (1S)-7-nitro-2-[1-(3-ethoxy-4-methoxyphenyl)-2-(methylsulfonyl)ethyl]isoindolin-1-one (1S)-7-nitro-2-[1-(3-ethoxy-4-methoxyphenyl)-2-(methylsulfonyl)ethyl]isoindolin-1-one was prepared by the following procedure. A mixture of methyl 2-bromomethyl-6-nitrobenzoate (100.0 g, 365 mmol, prepared previously in Example 5.7.2), (1S)-1-(3-ethoxy-4-methoxyphenyl)-2-methanesulfonylethylamine (104.7 g, 383 mmol, prepared previously in Example 5.7.3), sodium hydrogen carbonate (67.5 g, 8.03 moles, from Aldrich Chemicals) and dimethyl formamide (500 mL) was charged into a 1-L 3-necked flask at room temperature under nitrogen. The reaction mixture was gradually heated to an internal temperature of 70-75° C. for two hours until there was less than <2% of unreacted methyl 2-bromomethyl-6-nitrobenzoate. The reaction mixture was gradually heated to an internal temperature of 95-100° C. for 18 hours. The reaction mixture was cooled to 20-25° C. and transferred to an 1-L addition funnel. After purified water (1500 mL) was charged into a 5-L 3-necked flask, the reaction mixture in the addition funnel was added into water in the 5-L 3-necked flask at room temperature over 1-2 hours maintaining an internal temperature below 30° C. The reaction mixture was stirred for 2 hours at room temperature. The solid was filtered out under vacuum, washed with water (3×300 mL) and methanol (2×400 mL), and then charged into a 2-L 3-necked flask followed by methanol (1000 mL). The mixture was refluxed for 1 hour. The mixture was cooled to room temperature. The solid was collected by filtration under vacuum, washed with 200 mL methanol (2 vol), and dried to a constant weight at 40-45° C. under a vacuum at 100-120 torr. The yield of (1S)-7-nitro-2-[1-(3-ethoxy-4-methoxyphenyl)-2-(methylsulfonyl)ethyl] isoindolin-1-one was 123.0 g (78%), based on 100.0 g input of methyl 2-bromomethyl-6-nitrobenzoate. The product was found to have a purity of >99% measured by HPLC based on area percentage, and a water content of <0.1% measured by Karl Fisher titration Alternative Preparation of (1S)-7-nitro-2-[1-(3-ethoxy-4-methoxyphenyl)-2-(methylsulfonyl)ethyl] isoindolin-1-one (1S)-7-nitro-2-[1-(3-ethoxy-4-methoxyphenyl)-2-(methylsulfonyl)ethyl]isoindolin-1-one was also prepared by the following procedure. A mixture of methyl 2-bromomethyl-6-nitrobenzoate (100.0 g, 365 mmol, prepared previously in Example 5.7.2), (1S)-1-(3-ethoxy-4-methoxyphenyl)-2-methanesulfonyl-ethylamine (104.7 g, 383 mmol, prepared previously in Example 5.7.3), and potassium carbonate powder (100.8 g, 730 mmol, from Aldrich Chemicals) was suspended in acetonitrile (500 mL) at room temperature. The reaction mixture was refluxed at 81-83° C. for about two hours until there was less than 2% of unreacted methyl 2-bromomethyl-6-nitrobenzoate. After the reaction mixture was cooled to 45-50° C., methanol (200 mL) was charged over 5-10 minutes. After the mixture was allowed to cool to 20-25° C. and stirred for 2 hours, deionized water (1.40 L) was charged over 0.5-1 hour and stirred at 20-25° C. for 30 minutes and at 0-5° C. for 1-2 hours. The solid was filtered, washed with deionized water (3×300 mL), and dried to <10% of water content as measured by Karl Fisher titration. The solid was suspended in methanol (750 mL) and refluxed for 1-1.5 hours. The suspension was cooled to 0-5° C. over 1.5-2 hours and kept at 0-5° C. for 1-1.5 hours. The solid was filtered, washed with 0-5° C. methanol (2×200 mL) and heptane (200 mL), and then dried at 40-45° C. under vacuum to a constant weight. The yield of (1S)-7-nitro-2-[1-(3-ethoxy-4-methoxyphenyl)-2-(methylsulfonyl)ethyl]isoindolin-1-one was 148.0 g (93%), based on 100.0 g input of methyl 2-bromomethyl-6-nitrobenzoate. The product was found to have a purity of >99% measured by HPLC based on area percentage, and a water content of <1.0% measured by Karl Fisher titration Preparation of Compound B A mixture of (1S)-7-nitro-2-[1-(3-ethoxy-4-methoxyphenyl)-2-(methylsulfonyl)ethyl]isoindolin-1-one (60 g, 138 mmol, prepared previously in Example 5.7.5), 10% Pd/C (50% wet, 2.4 g, 4 wt %, from Johnson Matthey, London, UK), ethyl acetate (780 mL) was charged into a Parr-vessel at room temperature under nitrogen. After the mixture was purged with nitrogen three times and with hydrogen three times, the reaction mixture was heated to 40° C. and then the heat was removed. The reaction mixture was stirred with hydrogen at a pressure between 40-45 psi over 4-6 hours until there was ≤3% of the hydroxylamine intermediate. The reaction mixture was cooled to 20-25° C. The reaction mixture was filtered through a celite bed (1 inch thickness) and then bed-washed with ethyl acetate (120 mL). The filtrate was transferred to a 3-L 3-necked flask equipped with a 50-mL addition funnel. After N,N-diisopropylethylamine (29 mL, 165 mmol) was charged into the flask, the addition funnel was charged with cyclopropylcarbonyl chloride (13.0 mL, 145 mmol, from Aldrich Chemicals). The cyclopropylcarbonyl chloride was added at room temperature over 1-2 hours at an internal temperature below 30° C. The reaction mixture was stirred for 2-4 hours at room temperature. After heptane (300 mL) was added, the reaction mixture was stirred for 4-6 hours. The solid was collected by filtration under vacuum, washed with 2N HCl (2×300 mL), water (2×300 mL) and then heptane (2×300 mL). The crude product was dried at 40-45° C. under a vacuum at 100-120 torr to a constant weight. The yield of crude Compound (1) was 58 g (88%), based on 60.0 g input of (1S)-7-nitro-2-[1-(3-ethoxy-4-methoxyphenyl)-2-(methylsulfonyl)ethyl]-isoindolin-1-one.

Recrystallization of Compound B

A mixture of crude Compound (1) (95.2 g, prepared previously in Example 5.7.6) and tetrahydrofuran (THF, 1.43 L) was charged into a 3 L flask at 20-25° C. under nitrogen. The suspension was heated to 60-65° C. until dissolution was achieved. The suspension was filtered at 45-50° C. and the solid was rinsed with 95 mL of THF prewarmed at 45-55° C. After about 950-1150 mL of THF was distilled off at normal pressure over 30-60 minutes, absolute ethanol (950 mL) was charged at 55-60° C. over 5-10 minutes. About 350-400 mL of solvents was removed at normal pressure until the internal temperature rose to 72-74° C. The resulting suspension was refluxed at 72-75° C. for 30-60 minutes, cooled to 20-25° C. over 1-2 hours and kept at 20-25° C. for another 1-2 hours. The solid was collected by filtration under vacuum, washed with absolute ethanol (240-280 mL) and heptane (240-280 mL), and then dried in tray at 50-55° C. in a vacuum at 130-140 torr to a constant weight. The yield of the off-white crystalline product was (88.0-91.0 g, 92-96%).

The compounds described herein may also be prepared according to the processes described in U.S. Patent Publication No. 2010/0168475, the disclosure of which is hereby incorporated by reference in its entirety.

Example 4: CONTROLLED RELEASE FORMULATIONS 1 TO 3

Compound A was formulated in 500 mg tablets by direct compression. The drug loading is 10%. The data below show the in vitro evaluation of the release profile and water uptake of expandable polymer systems for gastroretentive system and controlled release solid dosage.

|  | 500 mg | % |
|---|---|---|
| Formulation 1 | | |
| Compound A | 50 | 10 |
| POLYOX N-1105 | 180 | 36 |
| NaCl | 75 | 15 |
| Chitopharm S | 20 | 4 |
| Protanal LF 200M | 75 | 15 |
| Lactose | 62.5 | 12.5 |
| Ac-Di-Sol | 35 | 7 |
| Mg Stearate | 2.5 | 0.5 |
| total | 500 | 100 |
| Formulation 2 | | |
| Compound A | 50 | 10 |
| CMC 7L2P | 180 | 36 |
| NaCl | 75 | 15 |
| ChitoClear 3568 | 20 | 4 |
| Protanal LF 200M | 75 | 15 |
| Lactose | 62.5 | 12.5 |
| Ac-Di-Sol | 35 | 7 |
| Mg Stearate | 2.5 | 0.5 |
| total | 500 | 100 |
| Formulation 3 | | |
| Compound A | 50 | 10 |
| POLYOX 205 | 180 | 36 |
| NaCl | 75 | 15 |
| ChitoClear 3568 | 20 | 4 |
| Protanal LF 200M | 75 | 15 |
| Lactose | 62.5 | 12.5 |
| Ac-Di-Sol | 35 | 7 |
| Mg Stearate | 2.5 | 0.5 |
| total | 500 | 100 |

Drug Release Profiles of Formulations 1 to 3

Drug dissolution studies from tablets were carried out in 900 mL dissolution medium, 1% Tween 80 solution with 10 mM NaAc at pH 4.0, at 100 RPM using USP I basket method. The drug content in tablets was 10%. Results are shown in FIG. 1.

Swelling Profiles of Formulations 1 to 3

The swelling ratios of tablet Formulations 1 to 3 was determined by percent weight gain. Water uptake of the tablets was carried out in 500 mL solution at 37° C. with 10 mM NaAc at pH 4.0, using Distek Dissolution System.

| | % Weight Gain | | | |
|---|---|---|---|---|
| Formulation | 1 hr | 2 hr | 4 hr | 6 hr |
| 1 | 148 | 222 | 315 | 409 |
| 2 | 165 | 248 | 358 | 320 |
| 3 | 162 | 258 | 389 | 508 |

Example 5: CONTROLLED RELEASE FORMULATIONS 4 TO 7

Compound A was formulated in 500 mg tablets by direct compression. The drug loading is 10%. The data below show the in vitro evaluation of the release profile and water uptake of expandable polymer systems for gastroretentive system and controlled release solid dosage.

|  | 500 mg | % |
|---|---|---|
| Formulation 4 | | |
| Compound A | 50 | 10 |
| POLYOX N-12K | 250 | 50 |
| Lactose | 57.5 | 11.5 |
| Protanal LF 200M | 70 | 14 |
| Natrosol L Pharm | 70 | 14 |
| Mg Stearate | 2.5 | 0.5 |
| total | 500 | 100 |
| Formulation 5 | | |
| Compound A | 50 | 10 |
| POLYOX N-12K | 250 | 50 |
| Lactose | 57.5 | 11.5 |
| Protanal LF 200D | 70 | 14 |

-continued

|  | 500 mg | % |
|---|---|---|
| Natrosol L Pharm | 70 | 14 |
| Mg Stearate | 2.5 | 0.5 |
| total | 500 | 100 |

Formulation 6

| Compound A | 50 | 10 |
|---|---|---|
| POLYOX N-12K | 250 | 50 |
| Lactose | 57.5 | 11.5 |
| Gelcarin GP 379 | 70 | 14 |
| Natrosol L Pharm | 70 | 14 |
| Mg Stearate | 2.5 | 0.5 |
| total | 500 | 100 |

Formulation 7

| Compound A | 50 | 10 |
|---|---|---|
| POLYOX N-12K | 180 | 36 |
| Lactose | 57.5 | 11.5 |
| Chitopharm S | 70 | 14 |
| Protanal LF 200D | 70 | 14 |
| Natrosol L Pharm | 70 | 14 |
| Mg Stearate | 2.5 | 0.5 |
| total | 500 | 100 |

Drug Release Profiles of Formulations 4 to 7

Figure 2:
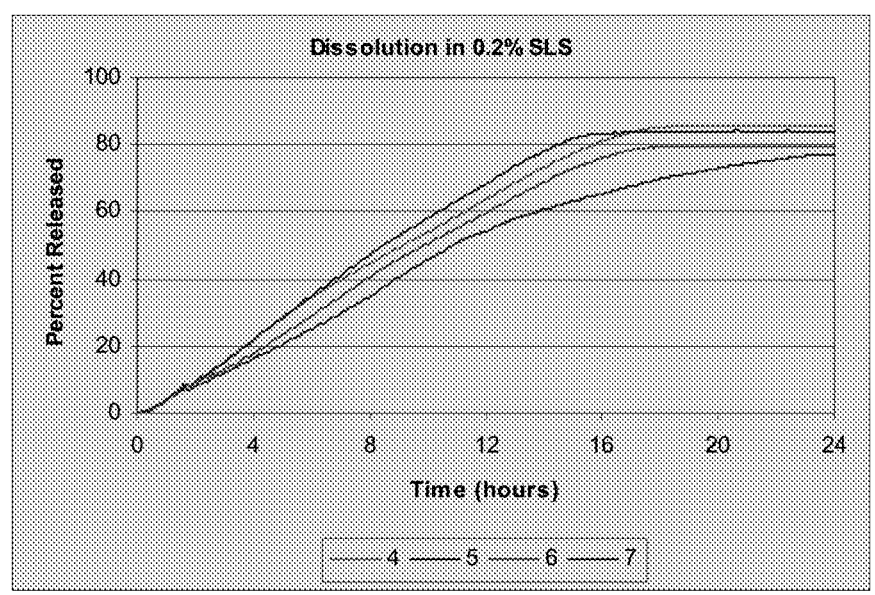
FIG. 2 shows the drug release profile of Compound A in Formulations 4 to 7 over 24 hours.

Drug dissolution studies from tablets were carried out in 900 mL dissolution medium, 0.2% SLS with 10 mM NaAc at pH 4.0, at 100 RPM using USP I basket method. Results are shown in FIG. 2.

Swelling Profiles of Formulations 4 to 7

The swelling ratios of tablet Formulations 4 to 7 was determined by percent weight gain. Water uptake of the tablets was carried out in 500 mL solution at 37° C. with 0.01 N HCl solution, using Distek Dissolution System.

| | % Weight Gain | | |
|---|---|---|---|
| Formulation | 1 hr | 2 hr | 6 hr |
| 4 | 132 | 176 | 249 |
| 5 | 147 | 180 | 249 |
| 6 | 139 | 176 | 209 |
| 7 | 156 | 252 | 664 |

Example 6

Controlled Release Formulations 8 to 11

Compound A was formulated in 250 mg tablets by direct compression. The drug loading is 20%. The data below show the in vitro evaluation of the release profile and water uptake of expandable polymer systems for gastroretentive system and controlled release solid dosage.

|  | 250 mg | % |
|---|---|---|
| | Formulation 8 | |
| Compound A | 50 | 20 |
| POLYOX N-12K | 82 | 32.8 |
| NaCl powder | 26 | 10.4 |
| Chitopharm M | 30 | 12 |
| Protanal LF 200M | 21 | 8.4 |
| Natrosol M Pharm | 21 | 8.4 |
| Avicel PH-102 | 19 | 7.6 |
| Mg Stearate | 1 | 0.4 |
| total | 250 | 100 |

Formulation 9

| Compound A | 50 | 20 |
|---|---|---|
| POLYOX N-12K | 85 | 34 |
| NaCl powder | 30 | 12 |
| Chitopharm S | 33 | 13.2 |
| Protanal LF 200M | 19 | 7.6 |
| Natrosol G Pharm | 32 | 12.8 |
| Mg Stearate | 1 | 0.4 |
| total | 250 | 100 |

Formulation 10

| Compound A | 50 | 20 |
|---|---|---|
| POLYOX N-12K | 85 | 34 |
| NaCl powder | 30 | 12 |
| Eudragit E PO | 33 | 13.2 |
| Protanal LF 200M | 19 | 7.6 |
| Natrosol G Pharm | 32 | 12.8 |
| Mg Stearate | 1 | 0.4 |
| total | 250 | 100 |

Formulation 11

| Compound A | 50 | 20 |
|---|---|---|
| POLYOX N-12K | 85 | 34 |
| NaCl powder | 15 | 6 |
| Eudragit E PO | 33 | 13.2 |
| Lactose | 20 | 8 |
| CMC 7LF | 19 | 7.6 |
| Natrosol G Pharm | 27 | 10.8 |
| Mg Stearate | 1 | 0.4 |
| total | 250 | 100 |

Drug Release Profiles of Formulations 8 to 11

Figure 3:
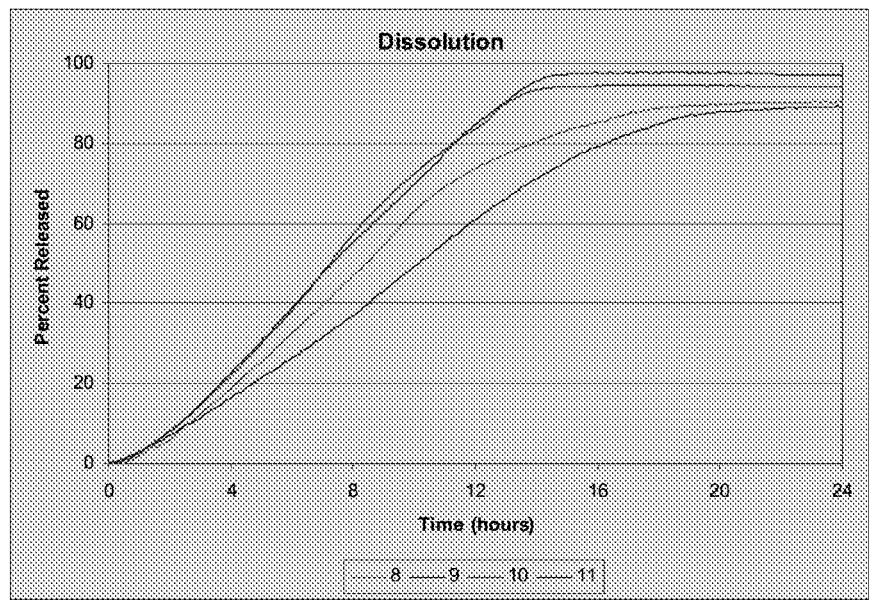
FIG. 3 shows the drug release profile of Compound A in Formulations 8 to 11 over 24 hours.

Drug dissolution studies from tablets were carried out in 900 mL dissolution medium, 0.2% SLS with 10 mM NaAc at pH 4.0, at 100 RPM using USP I basket method. Results are shown in FIG. 3.

Swelling Profiles of Formulations 8 to 11

The swelling ratios of tablet Formulations 8 to 11 was determined by percent weight gain. Water uptake of the tablets was carried out in 500 mL solution at 37° C. with 0.01 N HCl solution, using Distek Dissolution System.

| | % Weight Gain | |
|---|---|---|
| Formulation | 1 hr | 2 hr |
| 8 | 197 | 252 |
| 9 | 175 | 219 |
| 10 | 175 | 164 |
| 11 | 186 | 187 |

Example 7

Controlled Release Formulations 12 to 15

Data shown below show the in vitro release profile of Formulations 12 to 15, which are controlled release tables without swelling effects. The compositions of Formulations 12 to 15 are in weight percent. The drug loading is 20%.

| | Formulation | | | |
|---|---|---|---|---|
| | 12 | 13 | 14 | 15 |
| Compound A | 20 | 20 | 20 | 20 |
| HPMC E5LV | | 20 | | |
| HPMC K100LV | 30 | 10 | 30 | |
| Kollidon SR | | | | 10 |
| Polyox N-80 | | | | |
| Polyox 1105 | | | | |
| MCC | 49.5 | | | |
| Lactose | | 49.5 | 49.5 | 69.5 |
| Mg Stearate | 0.5 | 0.5 | 0.5 | 0.5 |

Drug Release Profiles of Formulations 12 to 15

Figure 4:
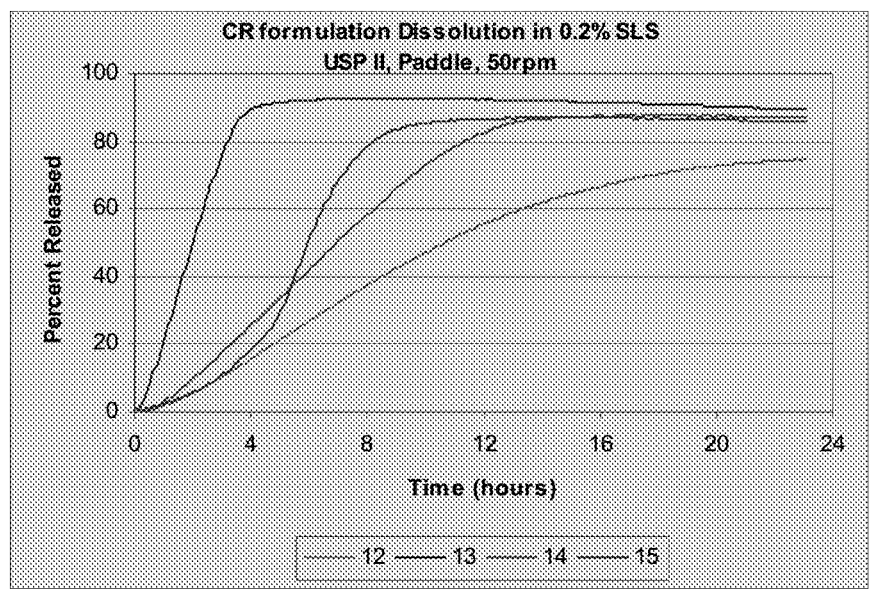
FIG. 4 shows the drug release profile of Compound A in Formulations 12 to 15 over 24 hours.

Drug dissolution studies from tablets were carried out in 900 mL dissolution medium, 0.2% SLS with 10 mM NaAc at pH 4.0, at 50 RPM using USP II paddle method. Results are shown in FIG. 4.

Example 8

Controlled Release Formulations 16 to 21

Data shown below show the in vitro release profile of Formulations 16 to 21, which are controlled release tables without swelling effects. The compositions of Formulations 16 to 21 are in weight percent. The drug loading is 20%.

| | Formulation | | | | | |
|---|---|---|---|---|---|---|
| | 16 | 17 | 18 | 19 | 20 | 21 |
| Compound A | 20 | 20 | 20 | 20 | 10 | 10 |
| HPMC E5LV | 10 | | | | 20 | |
| HPMC K100LV | 20 | | | | 10 | 30 |
| Kollidon SR | | | | 20 | | |
| Polyox N-80 | | 20 | | | | |
| Polyox 1105 | | 10 | 30 | | | |
| MCC | | | | | | |
| Lactose | 49.5 | 49.5 | 49.5 | 59.5 | 59.5 | 59.5 |
| Mg Stearate | 0.5 | 0.5 | 0.5 | 0.5 | 0.5 | 0.5 |

Drug Release Profiles of Formulations 16 to 21

Figure 5:
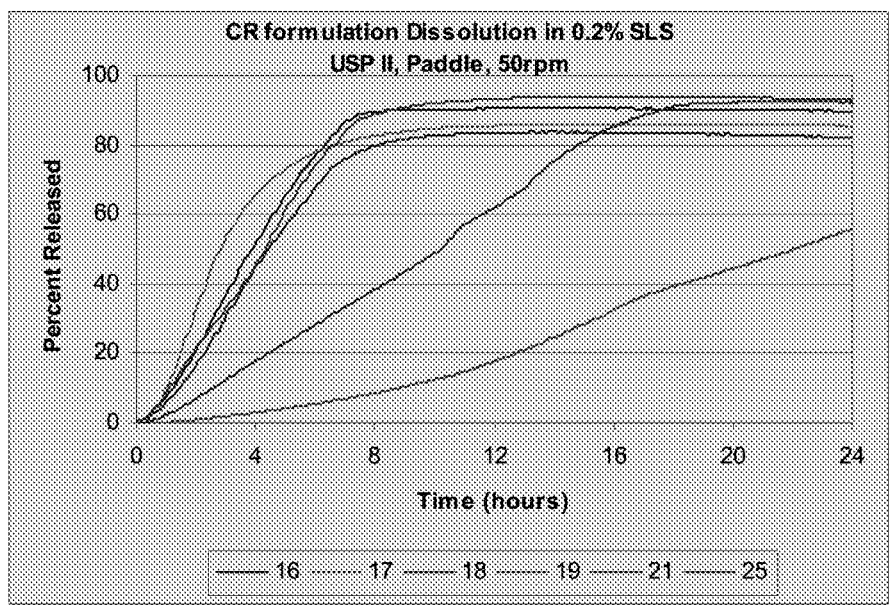
FIG. 5 shows the drug release profile of Compound A in Formulations 16 to 25 over 24 hours.
Figure 6:
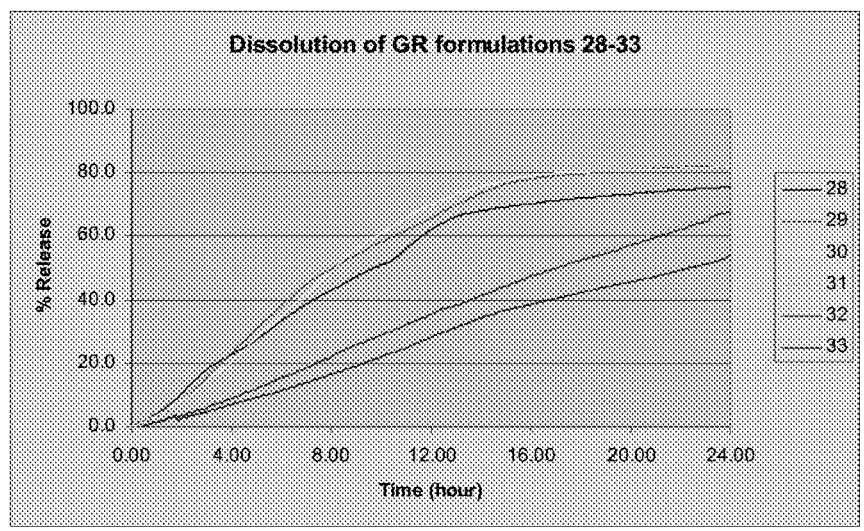
FIG. 6 shows the drug release profile of Compound A in Formulations 28 to 33 over 24 hours.
Figure 7:
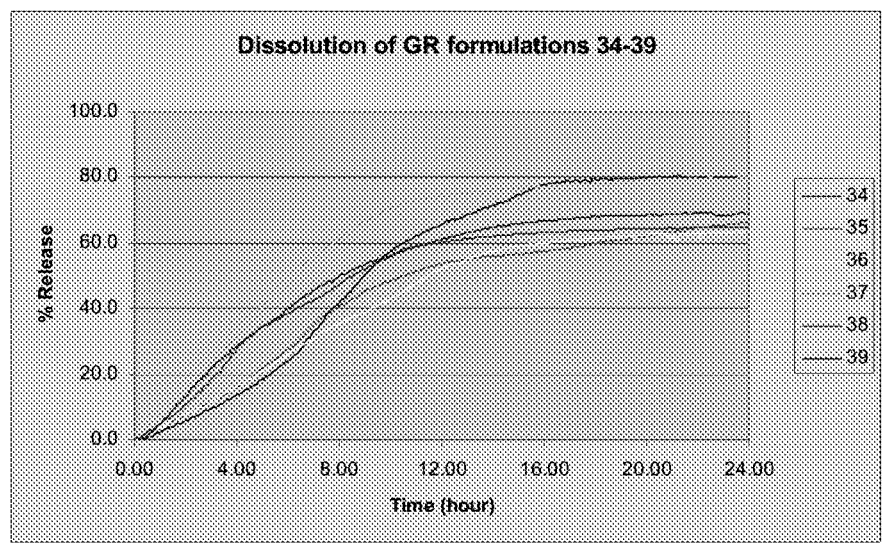
FIG. 7 shows the drug release profile of Compound A in Formulations 34 to 39 over 24 hours.
Figure 8:
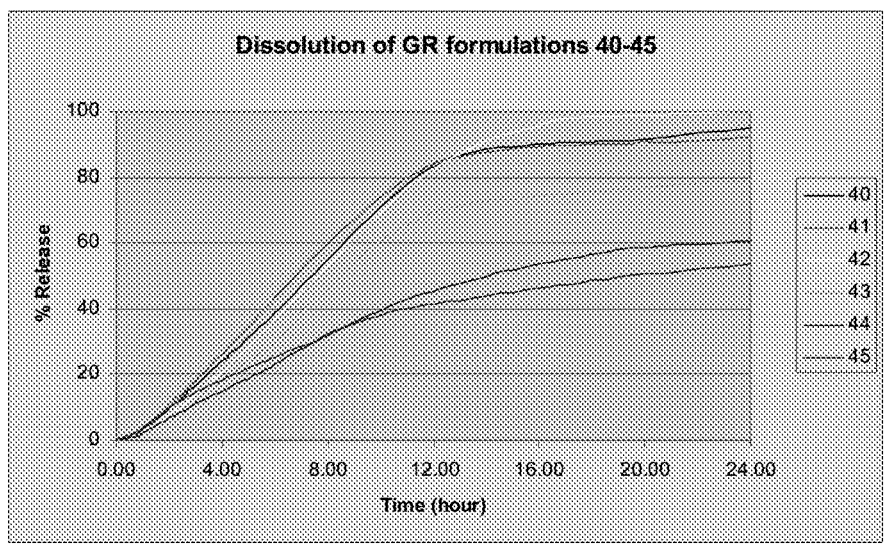
FIG. 8 shows the drug release profile of Compound A in Formulations 40 to 45 over 24 hours.
Figure 9:
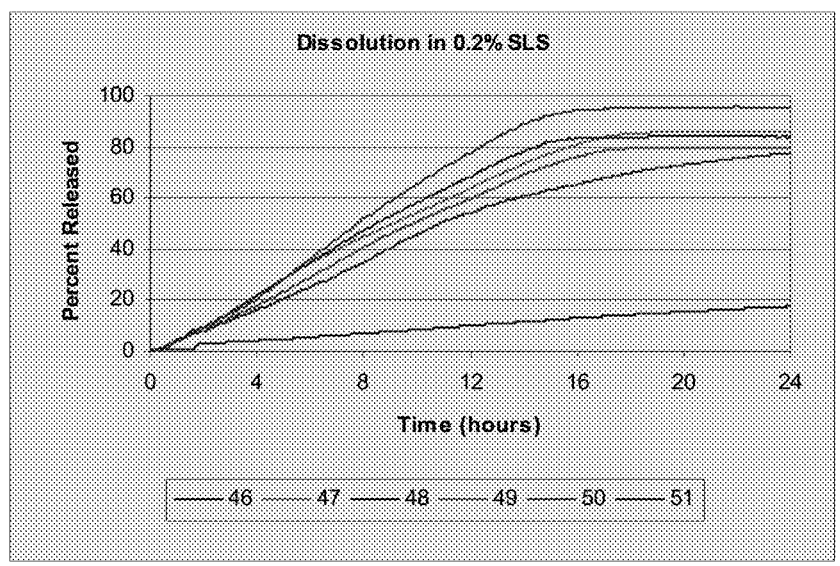
FIG. 9 shows the drug release profile of Compound A in Formulations 46 to 51 over 24 hours.
Figure 10:
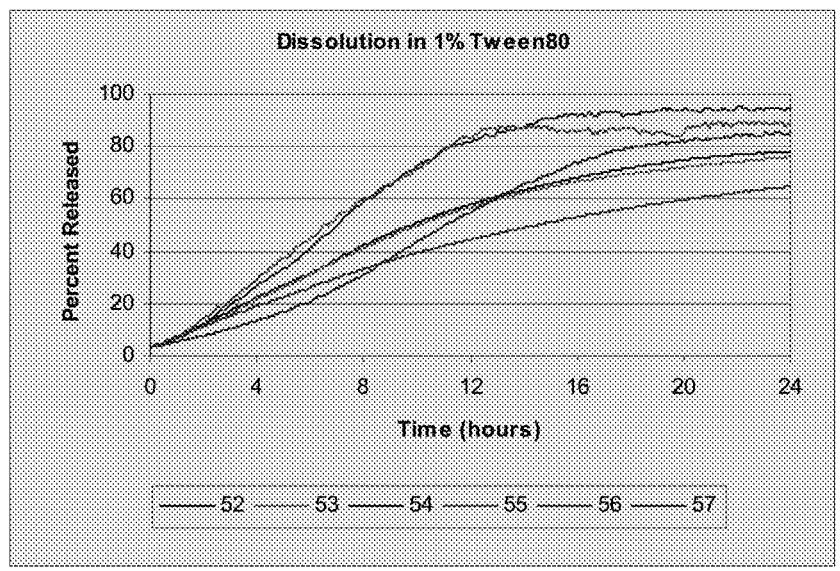
FIG. 10 shows the drug release profile of Compound A in Formulations 52 to 57 over 24 hours.
Figure 11:
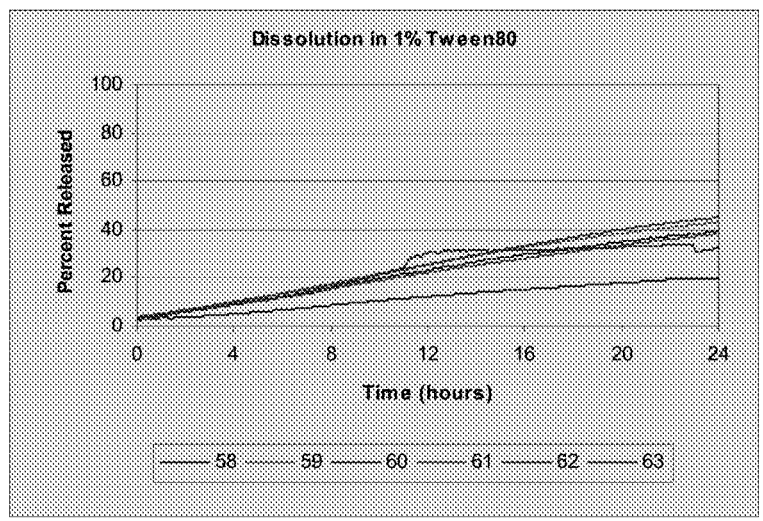
FIG. 11 shows the drug release profile of Compound A in Formulations 58 to 63 over 24 hours.
Figure 12:
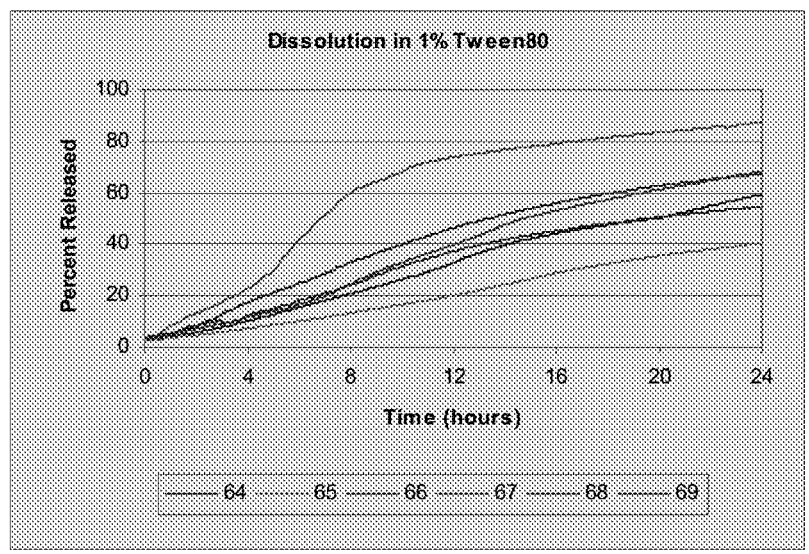
FIG. 12 shows the drug release profile of Compound A in Formulations 64 to 69 over 24 hours.
Figure 13:
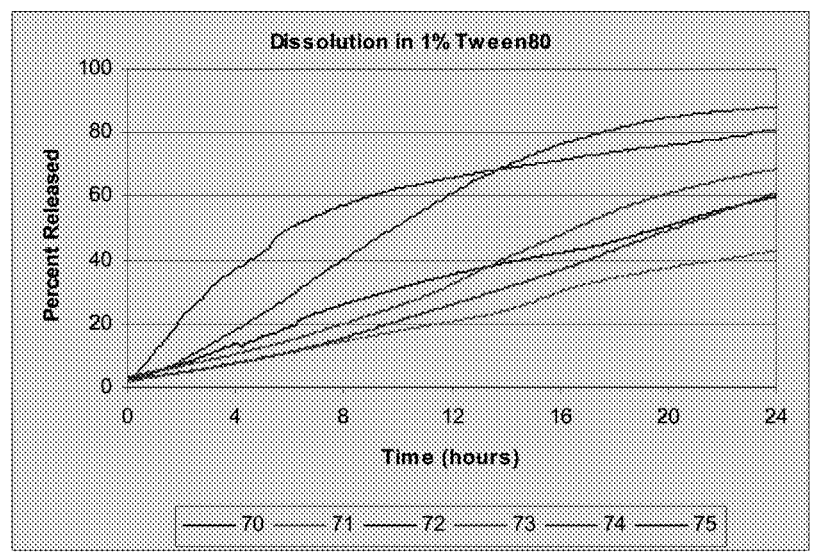
FIG. 13 shows the drug release profile of Compound A in Formulations 70 to 75 over 24 hours.
Figure 14:
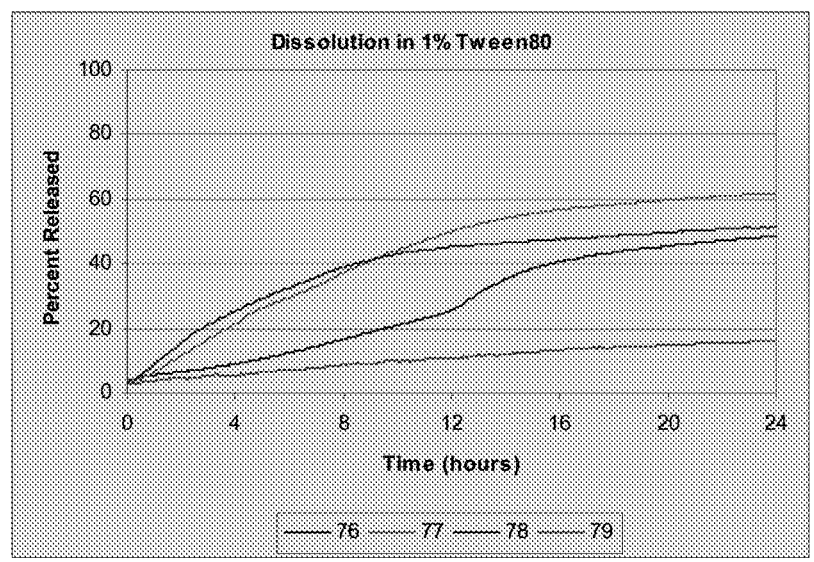
FIG. 14 shows the drug release profile of Compound A in Formulations 76 to 79 over 24 hours.
Figure 15:
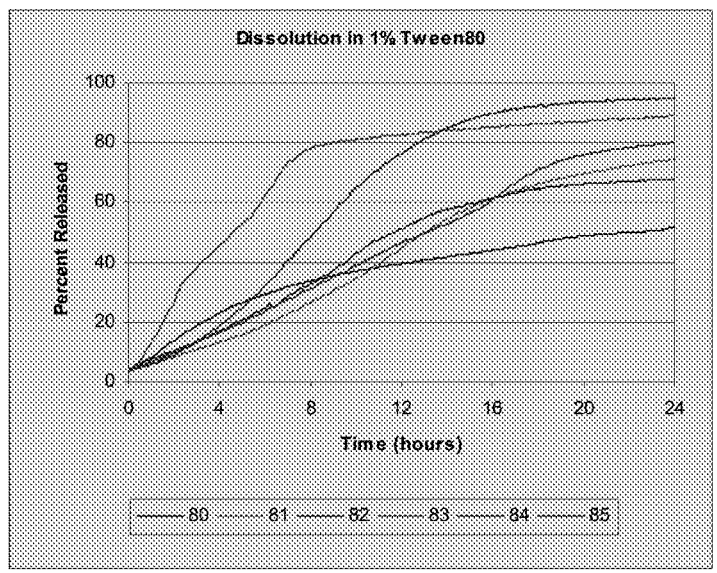
FIG. 15 shows the drug release profile of Compound A in Formulations 80 to 85 over 24 hours.
Figure 16:
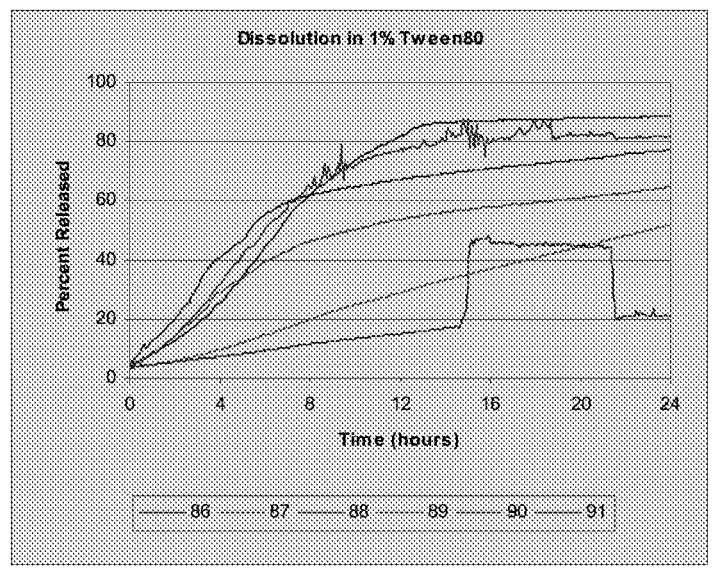
FIG. 16 shows the drug release profile of Compound A in Formulations 86 to 91 over 24 hours.
Figure 17:
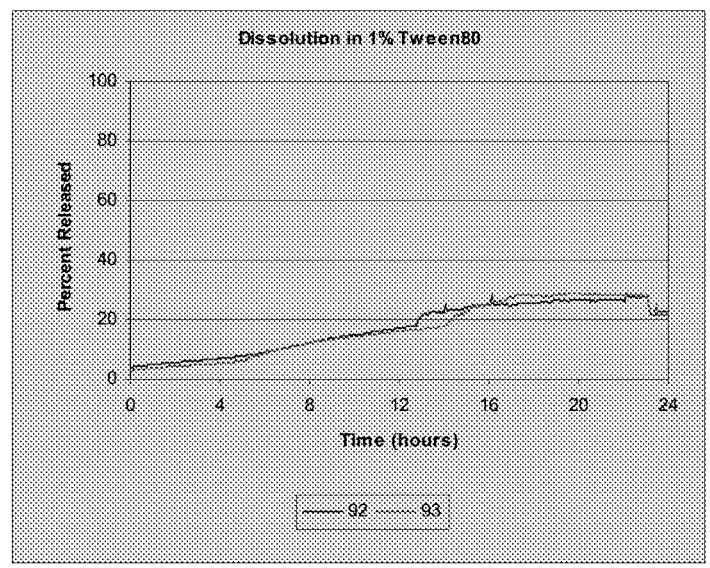
FIG. 17 shows the drug release profile of Compound A in Formulations 92 to 93 over 24 hours.

Drug dissolution studies from tablets were carried out in 900 mL dissolution medium, 0.2% SLS with 10 mM NaAc at pH 4.0, at 50 RPM using USP II paddle method. Results are shown in FIG. 5.

Example 9

Additional Controlled Release Formulations

The tables below present additional formulations of Compound A which were prepared and tested according to methods described herein for percent weight gain and percent drug release.

| | Formulation | | | | | |
|---|---|---|---|---|---|---|
| | #28 | #29 | #30 | #31 | #32 | #33 |
| Compound A | 20 | 20 | 20 | 20 | 20 | 20 |
| Polyox | 34 $^a$ | 34 $^a$ | 32.8 $^a$ | 30.4 $^b$ | 30.4 $^b$ | 34.4 $^b$ |
| NaCl Powder | 12 | 6 | 10.4 | 8.8 | 8.8 | |
| Chitopharm M | 13.2 | 13.2 | 12 | 13.2 | 13.2 | 13.2 |
| Protanal LF200M | 7.6 | | 8.4 | 7.6 | | 9.2 |
| Natrosol | 12.8 $^c$ | 10.8 $^d$ | 8.4 $^d$ | 12 $^d$ | 12 $^d$ | 9.2 $^d$ |
| Filler | 8 $^e$ | 7.6 $^f$ | 7.6 $^f$ | 7.6 $^f$ | | 13.6 $^e$ |
| CMC 7LF | | 7.6 | | | 7.6 | |
| Mg Stearate | 0.4 | 0.4 | 0.4 | 0.4 | 0.4 | 0.4 |

$^a$ Polyox N-12K
$^b$ Polyox 301
$^c$ Natrosol L
$^d$ Natrosol M
$^e$ Lactose
$^f$ Avicel

| | Formulation | | | | | |
|---|---|---|---|---|---|---|
| | #34 | #35 | #36 | #37 | #38 | #39 |
| Compound A | 20 | 20 | 20 | 20 | 20 | 20 |
| Polyox | 34 $^a$ | 33.2 $^a$ | 33.2 $^a$ | 33.2 $^a$ | 30.4 $^b$ | 34.4 $^c$ |
| NaCl Powder | 12 | 6 | 6 | 6 | 8.8 | |
| Chitopharm | 13.2 $^d$ | 13.2 $^e$ | 13.2 $^e$ | 13.2 $^e$ | 13.2 $^e$ | 13.2 $^e$ |
| Protanal LF200M | 7.6 | | 7.2 | | | 9.2 |
| Natrosol | 12.8 $^f$ | 8 $^g$ | 8 $^g$ | 8 $^g$ | 12 $^g$ | 9.2 $^g$ |
| Filler | | 8 $^h$ | 8 $^h$ | 8 $^h$ | 7.6 $^h$ | 13.6 $^h$ |
| CMC 7LF | | 7.2 | | 7.2 | 7.6 | |
| Surfactant | | 4 $^i$ | 4 $^j$ | 4 $^j$ | | |
| Mg Stearate | 0.4 | 0.4 | 0.4 | 0.4 | 0.4 | 0.4 |

$^a$ Polyox N-12K
$^b$ Polyox N-205 G
$^c$ Polyox N-1105
$^d$ Chitopharm S
$^e$ Chitopharm M
$^f$ Natrosol G
$^g$ Natrosol M
$^h$ Lactose
$^i$ SLS
$^j$ Pluronic F108

| Data | #28 | #29 | #30 | #31 | #32 | #33 | #34 | #35 | #36 | #37 | #38 | #39 |
|---|---|---|---|---|---|---|---|---|---|---|---|---|
| % Weight gain (2 hr,) | 241 | 217 | 252 | 313 | 273 | 296 | 219 | 213 | 245 | 258 | 216 | 285 |
| % Release (8 hr) | 43 | 50 | 49 | 22 | 22 | 16 | 42 | 41 | 36 | 61 | 48 | 50 |
| % Release (24 hr) | 76 | 82 | 82 | 68 | 68 | 54 | 80 | 66 | 64 | 80 | 65 | 69 |

| | Formulation | | | | | |
|---|---|---|---|---|---|---|
| | #40 | #41 | #42 | #43 | #44 | #45 |
| Compound A | 20 | 20 | 20 | 20 | 20 | 20 |
| Polyox N-K12 | 34 | 34 | 34 | 34 | 34 | 34 |
| NaCl Powder | 12 | 12 | 12 | 6 | 6 | 6 |
| Eudragit | 13.2 $^a$ | 13.2 $^b$ | 13.2 $^c$ | 13.2 $^a$ | 13.2 $^b$ | 13.2 $^c$ |
| Protanal LF200M | 7.6 | 7.6 | 7.6 | | | |
| Natrosol G | 12.8 | 12.8 | 12.8 | 10.8 | 10.8 | 10.8 |
| Lactose | | | | 8 | 8 | 8 |
| CMC 7LF | | | | 7.6 | 7.6 | 7.6 |
| Mg Stearate | 0.4 | 0.4 | 0.4 | 0.4 | 0.4 | 0.4 |

$^a$ Eudragit RLPO
$^b$ Eudragit RSPO
$^c$ Eudragit EPO

| Formulation | | | | | | |
|---|---|---|---|---|---|---|
| | #46 | #47 | #48 | #49 | #50 | #51 |
| Compound A | 20 | 20 | 20 | 20 | 20 | 20 |
| Polyox N-K12 | 50 | 50 | 50 | 50 | 50 | 36 |
| Chitopharm S | 14 | | | | | 14 |
| Protanal | | 14 [a] | 14 [b] | | | 14 [b] |
| Natrosol L | 14 | 14 | 14 | 14 | 14 | 14 |
| Gelcarin | | | | 14 [a] | 14 [d] | |
| Lactose | 11.5 | 11.5 | 11.5 | 11.5 | 11.5 | 11.5 |
| Mg Stearate | 0.5 | 0.5 | 0.5 | 0.5 | 0.5 | 0.5 |

[a] Protanal LF200D
[b] Protanal LF200M
[c] Gelcarin 379
[d] Gelcarin 209

| Data | #40 | #41 | #42 | #43 | #44 | #45 | #46 | #47 | #48 | #49 | #50 | #51 |
|---|---|---|---|---|---|---|---|---|---|---|---|---|
| % Weight gain (2 hr, HCl) | 175 | 173 | 164 | 181 | 188 | 187 | 147 | 176 | 180 | 176 | 175 | 252 |
| % Weight gain (6 hr, HCl) | 115 | 102 | 143 | 150 | 150 | 149 | 113 | 249 | 249 | 209 | 142 | 664 |
| % Release (8 hr) | 55 | 60 | 54 | 47 | 32 | 33 | 28 | 33 | 37 | 39 | 44 | 18 |
| % Release (24 hr) | 95 | 92 | 100 | 79 | 54 | 61 | 67 | 86 | 83 | 94 | 94 | 36 |

| Formulation | | | | | | |
|---|---|---|---|---|---|---|
| | #52 | #53 | #54 | #55 | #56 | #57 |
| Compound A | 10 | 10 | 10 | 10 | 10 | 10 |
| Polyox N-10 | 13.5 | 13.5 | 13.5 | 13.5 | | 15.5 |
| Polyox N-1105 | 36 | 36 | 36 | 60 | 36 | 37 |
| Soluplus | | | | | 13.5 | |
| NaCl | 10 | 10 | 10 | 10 | 10 | 10 |
| Chitopharm S | 6 | 6 | 6 | | 6 | 3 |
| Protanal | 18 [a] | 18 [b] | 12 [b] | | 18 [b] | |
| Citric Acid | | | 6 | | | |
| Gelcarin | | | | | | 18 |
| Avicel PH102 | 6 | 6 | 6 | 6 | 6 | 6 |
| Mg Stearate | 0.5 | 0.5 | 0.5 | 0.5 | 0.5 | 0.5 |

[a] Protanal LF200 M
[b] Protanal LF120 M

| Formulation | | | | | | |
|---|---|---|---|---|---|---|
| | #58 | #59 | #60 | #61 | #62 | #63 |
| Compound A | 10 | 10 | 10 | 10 | 10 | 10 |
| Polyox N-12K | 40 | 40 | 40 | 40 | 40 | 40 |
| NaCl | 15 | 15 | 15 | 15 | 15 | 15 |
| Chitopharm S | | | | | 10 | 10 |
| Chitoclear | 10 [a] | 10 [b] | 10 [c] | 10 [d] | | |
| Protanal LF200M | 16 | 16 | 16 | 16 | 16 | 6 |
| Gelcarin GP379 | | | | | | 10 |
| Avicel PH102 | 5.5 | 5.5 | 5.5 | 5.5 | 5.5 | 5.5 |
| Ac-Di-Sol | 3 | 3 | 3 | 3 | 3 | 3 |
| Mg Stearate | 0.5 | 0.5 | 0.5 | 0.5 | 0.5 | 0.5 |

[a] Chitoclear 3568
[b] Chitoclear 2832
[c] Chitoclear 3504
[d] Chitoclear 3548

| Data | #52 | #53 | #54 | #55 | #56 | #57 | #58 | #59 | #60 | #61 | #62 | #63 |
|---|---|---|---|---|---|---|---|---|---|---|---|---|
| % Weight gain (2 hr, pH 4) | 188 | 195 | 148 | 134 | 194 | 173 | 273 | 233 | 257 | 265 | 210 | 200 |
| % Weight gain (6 hr, pH 4) | 410 | 411 | 171 | 94 | 428 | 265 | 621 | 554 | 609 | 590 | 459 | 362 |
| % Release (8 hr) | 42 | 41 | 59 | 60 | 33 | 31 | 9 | 18 | 15 | 16 | 17 | 16 |
| % Release (24 hr) | 78 | 76 | 95 | 89 | 65 | 86 | 20 | 43 | 39 | 38 | 45 | 32 |

| Formulation | | | | | | |
|---|---|---|---|---|---|---|
| | #64 | #65 | #66 | #67 | #68 | #69 |
| Compound A | 10 | 10 | 10 | 10 | 10 | 10 |
| Polyox N-1105 | 36 | | 36 | | | |
| NaCl | 15 | 15 | 15 | 15 | 15 | 15 |
| Chitopharm S | | | 4 | | | |
| Chitoclear 3568 | 4 | 4 | | 4 | 4 | 4 |
| Protanal | 15 | 15 | 15 | 15 | 15 | 15 |
| Swelling Agent | | 36 [a] | | 36 [b] | 36 [c] | 36 [d] |
| Lactose | 12.5 | 12.5 | 12.5 | 12.5 | 12.5 | 12.5 |
| Ac-Di-Sol | 7 | 7 | 7 | 7 | 7 | 7 |
| Mg Stearate | 0.5 | 0.5 | 0.5 | 0.5 | 0.5 | 0.5 |

[a] Natrosol M
[b] CMC 7L2P
[c] Polyox 205
[d] Natrosol G

| Formulation | | | | | | |
|---|---|---|---|---|---|---|
| | #70 | #71 | #72 | #73 | #74 | #75 |
| Compound A | 10 | 10 | 10 | 10 | 10 | 10 |
| Eudragit | | | | | 12 [a] | 12 [b] |
| Polyox N-1105 | 38 | 38 | | | | |
| Polyox N-12K | | | | | 38 | 38 |
| NaCl | 12 | 12 | 12 | 12 | 4 | 4 |
| Chitoclear 3568 | 4 | 4 | 4 | 4 | | |
| Protanal | 10 | 10 | 10 | 10 | | |
| Swelling Agent | | | 38 [c] | 38 [d] | 13.5 [e] | 13.5 [e] |
| Primojel | 10 | | | | | |
| Lactose | 15.5 | 16 | 15.5 | 15.5 | 12 | 12 |
| Ac-Di-Sol | | 10 | 10 | 10 | 10 | 10 |
| Mg Stearate | 0.5 | 0.5 | 0.5 | 0.5 | 0.5 | 0.5 |

[a] Eudragit EPO
[b] Eudragit E100
[c] CMC 7LF
[d] Natrosol G
[e] CMC 7L2P

| Data | #64 | #65 | #66 | #67 | #68 | #69 | #70 | #71 | #72 | #73 | #74 | #75 |
|---|---|---|---|---|---|---|---|---|---|---|---|---|
| % Weight gain (2 hr, pH 4) | 261 | 260 | 223 | 250 | 257 | 237 | 233 | 226 | 225 | 214 | 204 | 170 |
| % Weight gain (6 hr, pH 4) | 517 | 567 | 409 | 320 | 508 | 439 | 422 | 461 | 250 | 431 | 380 | 172 |
| % Release (8 hr) | 21 | 13 | 33 | 60 | 25 | 24 | 26 | 14 | 57 | 20 | 16 | 40 |
| % Release (24 hr) | 59 | 41 | 67 | 88 | 68 | 55 | 60 | 43 | 81 | 69 | 61 | 88 |

| Formulation | | | | | | |
|---|---|---|---|---|---|---|
| | #76 | #77 | #78 | #79 | #80 | #81 |
| Compound A | 6.7 | 6.7 | 6.7 | 6.7 | 6.7 | 6.7 |
| Polyox N-1105 | 36 | 18 | | 39 | | 10 |
| NaCl | 15 | 15 | 15 | 15 | 14 | 14 |
| Chitoclear 3568 | 4 | 4 | 4 | 15 | 4 | |
| Protanal | 15 | 15 | 15 | 4 | 7.2 | |
| Swelling Agent | | 18 [a] | 36 [a] | | 42.8 [b] | 32 [a] |
| Eudragit EPO | | | | | | 10 |
| Lactose | 15.8 | 15.8 | 15.8 | 15.8 | 14.8 | 14.8 |
| Ac-Di-Sol | 7 | 7 | 7 | 7 | 10 | 12 |
| Mg Stearate | 0.5 | 0.5 | 0.5 | 0.5 | 0.5 | 0.5 |

[a] CMC 7L2P
[b] CMC 7LF

| Formulation | | | | | | |
|---|---|---|---|---|---|---|
| | #82 | #83 | #84 | #85 | #86 | #87 |
| Compound A | 6.7 | 6.7 | 6.7 | 6.7 | 6.7 | 6.7 |
| Polyox N-1105 | | | 36 | 28 | | 25.1 |
| Polyox (other) | 33.6 [a] | | 14 [b] | 15.6 [b] | 10.7 [c] | |
| NaCl | 14 | 14 | 14 | 14 | 14.4 | 14 |
| Chitopharm S | 5.2 | 4 | 4 | 3.2 | 5.3 | 3.2 |
| Protanal | 12 [d] | 6.8 [d] | 12 [d] | | 17.1 [e] | |
| Swelling Agent | | 44 [f] | | 16 [g] | | 14.5 [g] |
| Lactose | 16 | 14 | 12.8 | 16 | 18.7 | 18 |
| MCC | | | | | 18.7 | 18 |
| Citric Acid | | | | | 8 | |
| Disintegrant | 12 [h] | 10 [i] | | | | |
| Mg Stearate | 0.5 | 0.5 | 0.5 | 0.5 | 0.5 | 0.5 |

[a] Polyox N80
[b] Polyox N10
[c] Polyox N12K
[d] Protanal LF200M
[e] Protanal LF120M
[f] CMC 7L2P
[g] Gelcarin 209
[h] Primojel
[i] Ac-Di-Sol

| Data | #76 | #77 | #78 | #79 | #80 | #81 | #82 | #83 | #84 | #85 | #86 | #87 |
|---|---|---|---|---|---|---|---|---|---|---|---|---|
| % Weight gain (2 hr, pH 4) | 226 | 233 | 235 | 204 | 234 | 199 | 179 | 214 | 196 | 179 | 162 | 173 |
| % Weight gain (6 hr, pH 4) | 459 | 432 | 405 | 408 | 323 | 170 | 376 | 192 | 338 | 239 | 228 | 316 |
| % Release (8 hr) | 17 | 37 | 39 | 9 | 34 | 27 | 33 | 78 | 31 | 49 | 62 | 20 |
| % Release (24 hr) | 48 | 62 | 51 | 16 | 52 | 75 | 68 | 89 | 80 | 95 | 89 | 52 |

| Formulation | | | | | | |
|---|---|---|---|---|---|---|
| | #88 | #89 | #90 | #91 | #92 | #93 |
| Compound A | 6.7 | 6.7 | 6.7 | 6.7 | 6.7 | 6.7 |
| Polyox N-750 | | | | | 20 | 10 |
| Polyox (other) | | | 14.4 [a] | 20 [b] | | 10 [c] |
| NaCl | 14 | 14 | 14 | 15 | 15 | 15 |
| Chitopharm S | 4 | | | | | |
| Chitoclear 3568 | | 4 | | 5 | 5 | 5 |
| Protanal LF200M | 6.8 | 12 | | 5 | 5 | 5 |
| Swelling Agent | 26.7 [d] | | 14.4 [e] | | | |
| Lactose | 14 | 14.4 | 16 | 47.8 | 47.8 | 47.8 |
| MCC | 16 | 14.4 | 16 | | | |
| Ac-Di-Sol | 10 | 10 | 10 | | | |
| Mg Stearate | 0.5 | 0.5 | 0.5 | 0.5 | 0.5 | 0.5 |

[a] Polyox N12K
[b] Polyox N-1105
[c] Polyox N10
[d] CMC 7L2P
[e] Gelcarin 379

| Data | #88 | #89 | #90 | #91 | #92 | #93 |
|---|---|---|---|---|---|---|
| % Weight gain (2 hr, pH 4) | 211 | 255 | 122 | 170 | — | — |
| % Weight gain (6 hr, pH 4) | 205 | 403 | 62 | 335 | — | — |
| % Release (8 hr) | 62 | 46 | 65 | 12 | 12 | 12 |
| % Release (24 hr) | 77 | 65 | 82 | 21 | 23 | 22 |

Example 10

Bilayer Tablet Formulations

Bilayer tablets were prepared to achieve pulsatile drug release and/or immediate release followed by controlled release. An immediate release layer with a controlled release layer was been prepared for the bilayer tablets. The bilayer tablet was prepared as follows: load the gastric retentive portion (750 mg) into the die and compress manually; load 100 mg the immediate-release layer (Table 1) on top of it; compress using a Carver Press.

TABLE 1

| Formulation of Immediate-Released Layer | |
|---|---|
| Compound A | 10.0 |
| Microcrystalline Cellulose | 26.25 |
| Lactose Monohydrate | 60.0 |
| Croscarmellose Sodium | 3.0 |
| Magnesium Stearate | 0.75 |
| Total | 100 |

Figure 18:
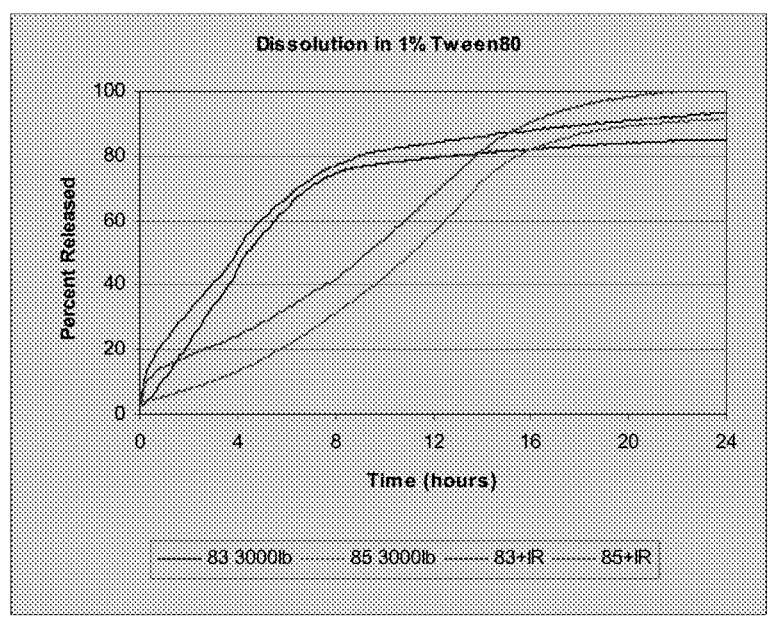
FIG. 18 shows the drug release profile of Compound A in bilayer tablets over 24 hours.

The release profiles of the bilayer tablets vs. 50 mg tablets at 3000 lb force are shown in FIG. 18.

Example 11

Gastric Retentive Bilayer Tablet Formulations

Bilayer tablets were prepared to combine the gastric retentive function and extended release profile in one dose unit. Formulations 13, 14 and 16 were each used as the extended release layer. The formulation of the gastric retentive layer is provided as follows in Table 2. The bilayer tablet was prepared as follows: load the gastric retentive portion (500 mg) into the die and compress manually; load 250 mg the extended-release layer (e.g., Formulation 13, 14 or 16) on top of it; compress using a Carver Press.

TABLE 2

| Formulation of Gastric-Retentive Layer | |
| --- | --- |
| Polyox 1105 | 16 |
| NaCl powder | 16 |
| Chitoclear 3568 | 12 |
| Protanal LF 200M | 12 |
| Avicel PH-102 | 43.5 |
| Mg Stearate | 0.5 |
| Total (%) | 100 |

Figure 19:
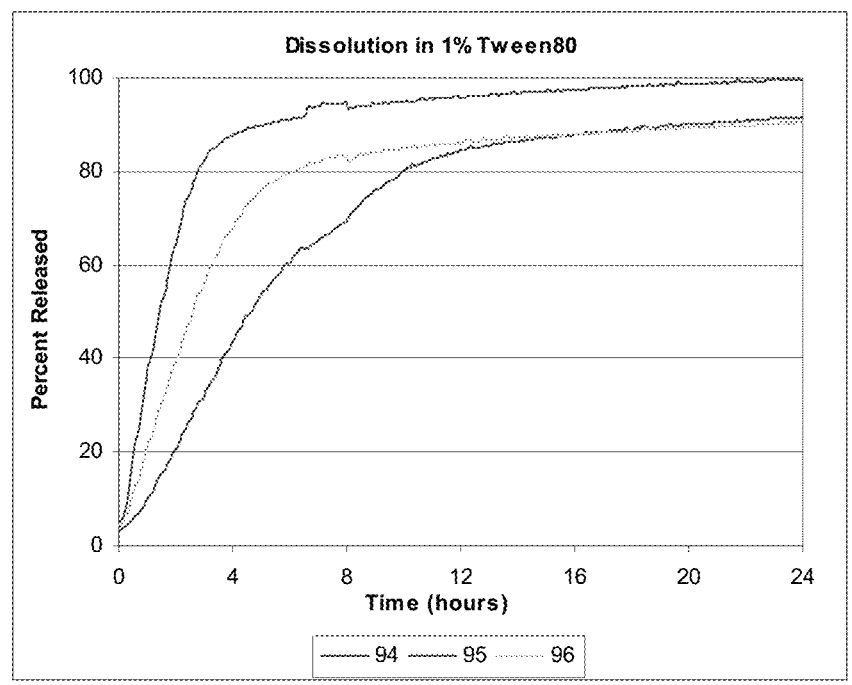
FIG. 19 shows the drug release profile of Compound A in Formulations 94 to 96 over 24 hours.
Figure 20A:
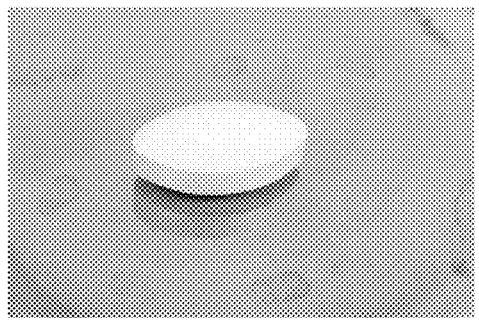
FIG. 20A shows gastroretentive Formulation 98.
Figure 20B:
FIG. 20B shows the floating properties of Formulation 98.
Figure 20C:
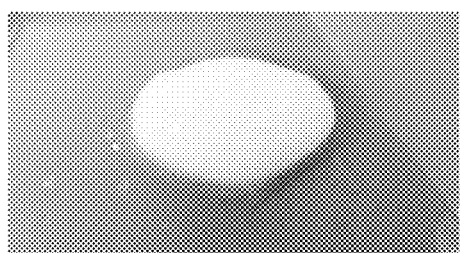
FIG. 20C shows the fast swelling properties of Formulation 98.
Figure 20D:
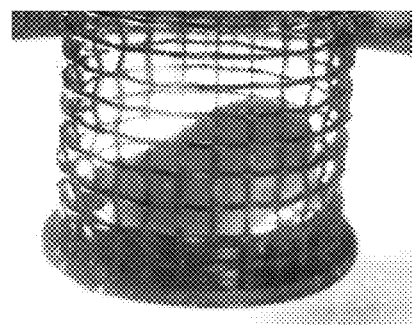
FIG. 20D shows the bioadhesive properties of Formulation 98.

Bi-layer gastric-retentive tablets were prepared as Formulations 94, 95 and 96 (Table 3). The release profiles of the bi-layer tablets are show in FIG. 19.

TABLE 3

| Formulation of Bi-layer Gastric-Retentive Tablets | | |
| --- | --- | --- |
| Formulation # | ER Layer (250 mg) | GR Layer (500 mg) |
| 94 | 13 | 217 |
| 95 | 14 | 217 |
| 96 | 16 | 217 |

Example 12

Gastric Retentive Tablet Formulations Comprising a Floating Agent

The table below present additional Gastric Retentive tablets comprising Compound A and sodium bicarbonate. The GR tablets are manufactured by compression of dry blend mixture. Alternatively, they can be prepared by roller compaction followed by compression. Coating is optional. The compositions of Formulations 97 to 100 are in weight percent. Formulations 97, 98, and 100 have a total weight of 750 mg. Formulation 99 has a total weight of 600 mg.

TABLE 4

| Formulations of Gastric-Retentive Tablets, weight | | | | |
| --- | --- | --- | --- | --- |
| | Formulation # | | | |
| | 97 | 98 | 99 | 100 |
| Compound A (Crystalline) | 10 | 10 | 10 | 10 |
| Eudragit EPO | 5 | 5 | 5 | 7 |
| Protanal LF200M | 19 | 19 | 19 | 19 |
| CMC 7L2P | 37 | 34.5 | 34.5 | 32.5 |
| Mannitol | 11.5 | 11.5 | 11.5 | 11.5 |
| Citric Acid | 6.5 | 8 | 8 | 8 |
| Sodium Bicarbonate | 4 | 5 | 5 | 5 |
| Ac-Di-Sol | 5 | 5 | 5 | 5 |
| Colloidal Silicon Dioxide | 0.5 | 0.5 | 0.5 | 0.5 |
| Mg Stearate | 1.5 | 1.5 | 1.5 | 1.5 |

Analysis of Formulation 98

Figure 25:
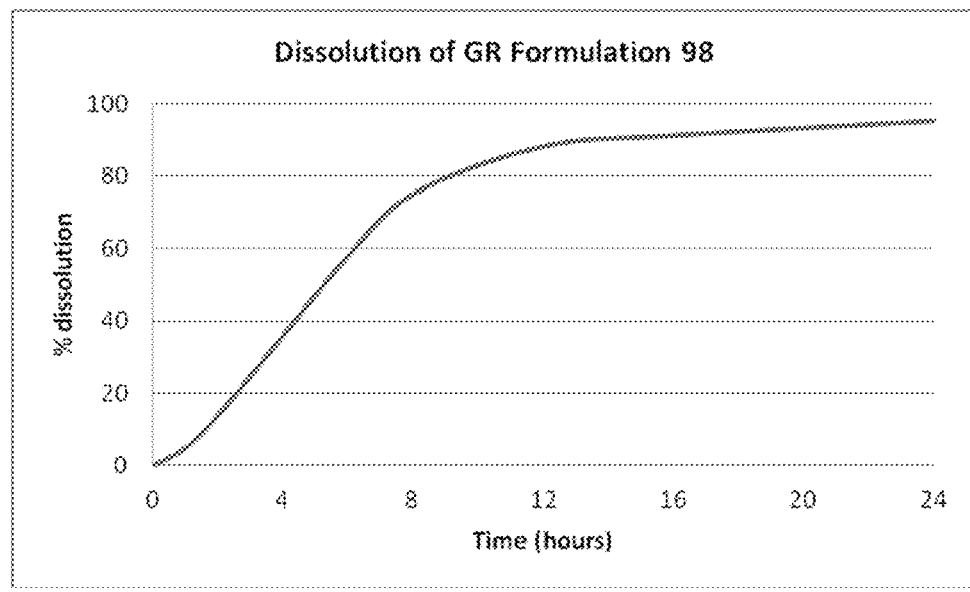
FIG. 25 shows the drug release profile of Compound A in Formulation 98 over 24 hours.
Figure 26:
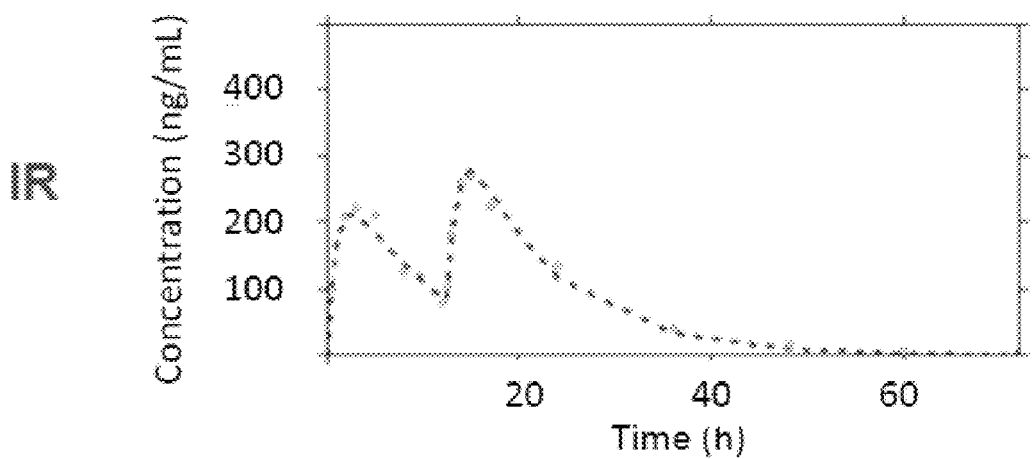
FIG. 26 shows the observed pharmacokinetic profile of Formulations 98 and 101 following a single dose, and a modeled pharmacokinetic profile following multiple doses, both at standard meal conditions.
Figure 26:
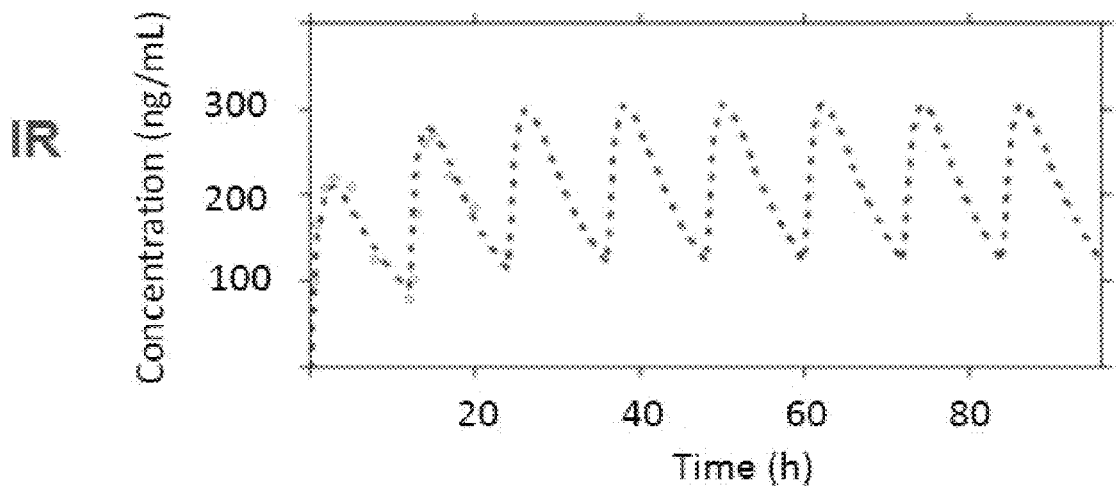
Figure 26:
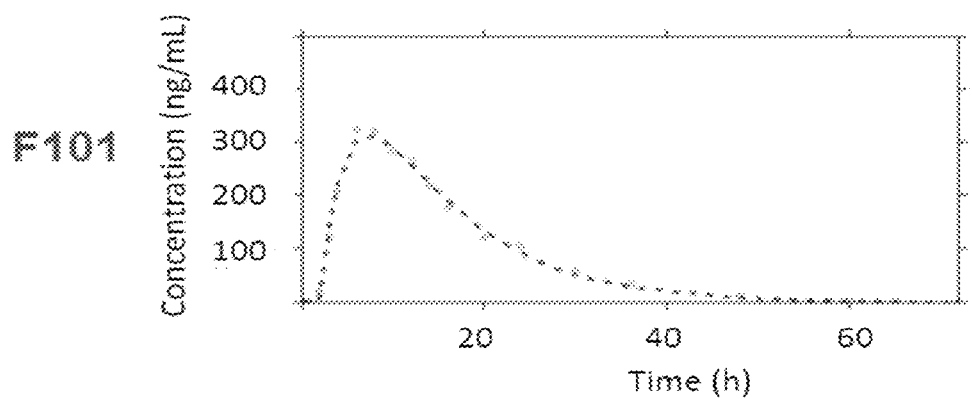
Figure 26:
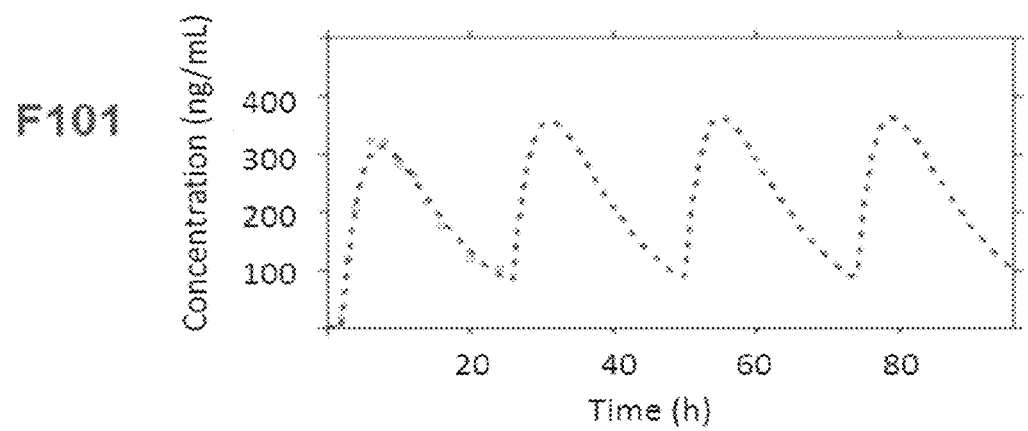
Figure 26:
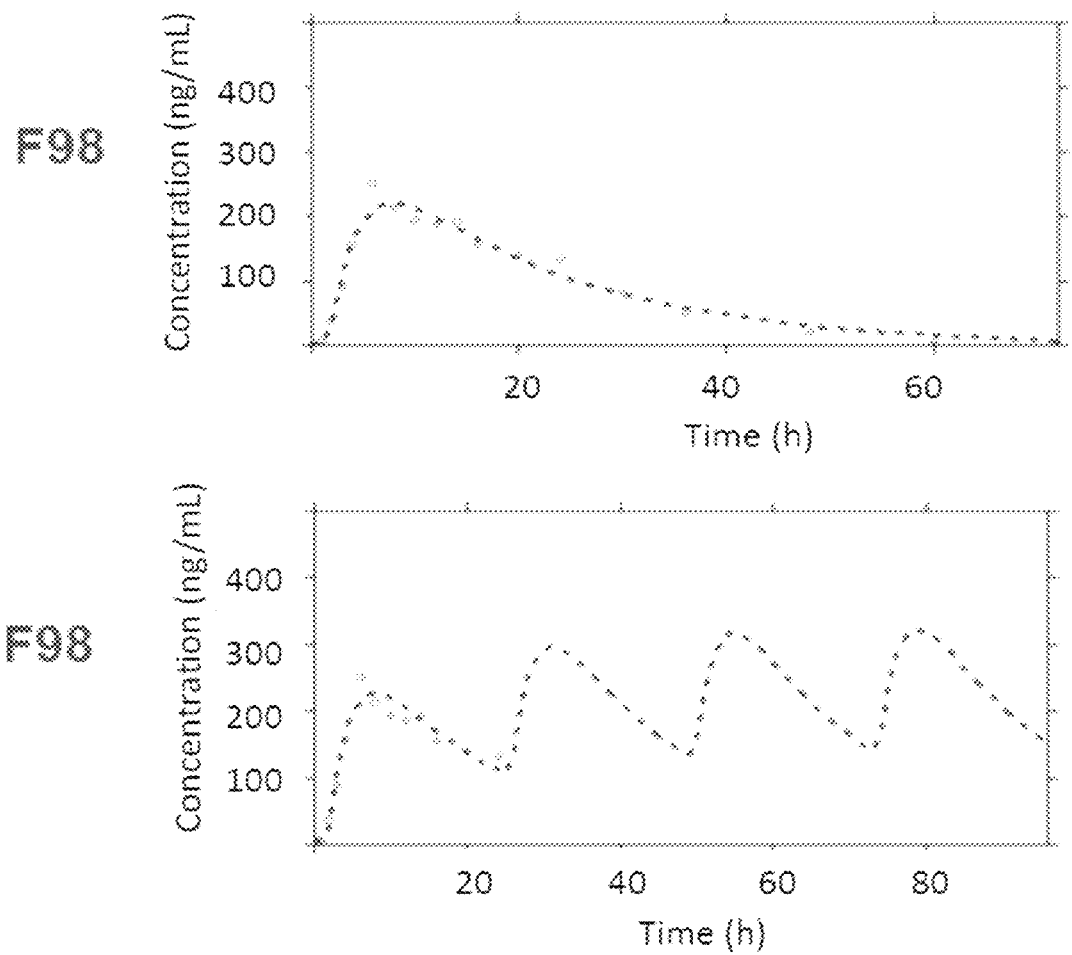

A drug dissolution study for Formulation 98 was carried out using an USP Apparatus 2 (Paddles), with a medium of 2% Tween 80 in 50 mM Sodium Acetate Buffer pH 4.5 (900 mL), with Rotation Speed of 75 RPM at 37.0±0.5° C. (Sampling Time: 1, 2, 4, 6, 8, 12, 16, and 24 hours). Results are shown in Table 5 and FIG. 25.

TABLE 5

| Dissolution of Formulation 98 | | | |
| --- | --- | --- | --- |
| Time (hours) | % dissolved Min | % dissolved Max | % dissolved Mean |
| 1 | 5 | 6 | 5 |
| 2 | 14 | 15 | 14 |
| 4 | 35 | 38 | 36 |
| 6 | 55 | 59 | 58 |
| 8 | 71 | 77 | 75 |
| 12 | 86 | 91 | 88 |
| 16 | 88 | 94 | 91 |
| 24 | 92 | 98 | 95 |

Pharmacokinetic Profile of Formulation 98

Figure 21:
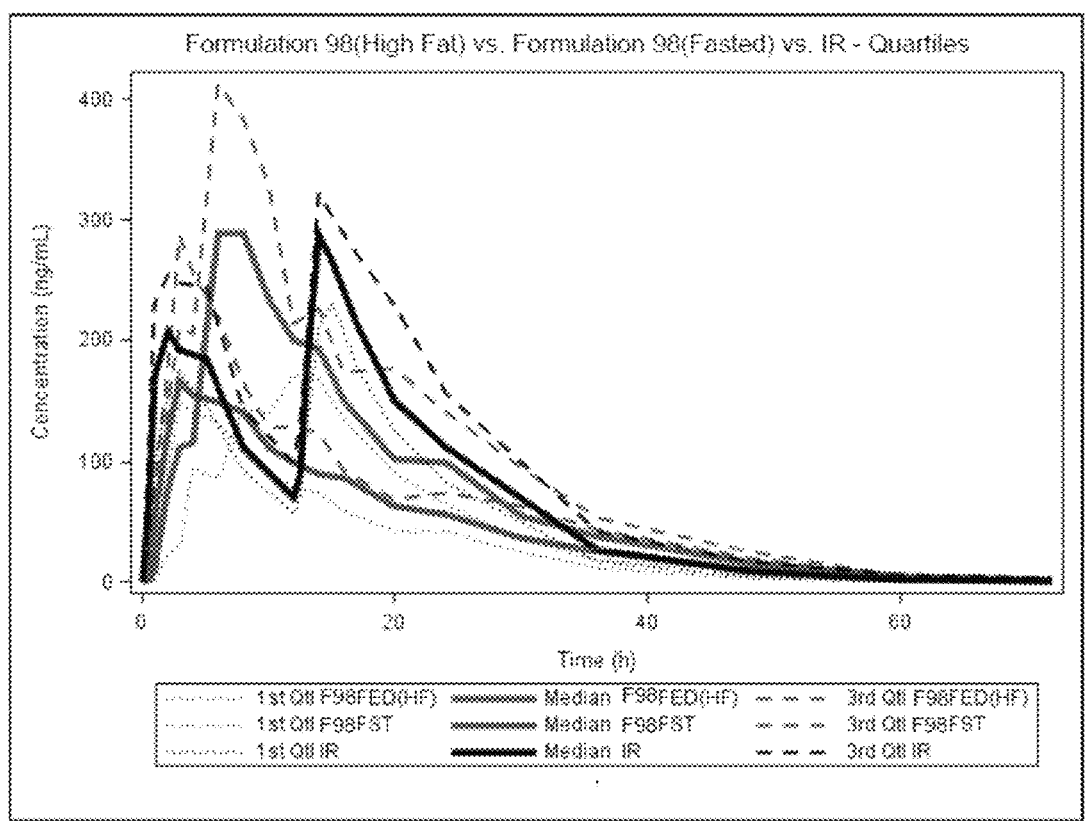
FIG. 21 shows the pharmacokinetic profile of Formulation 98 as compared to instant release (IR) formulation following a single oral dose under fasting and high fat meal conditions.
Figure 22:
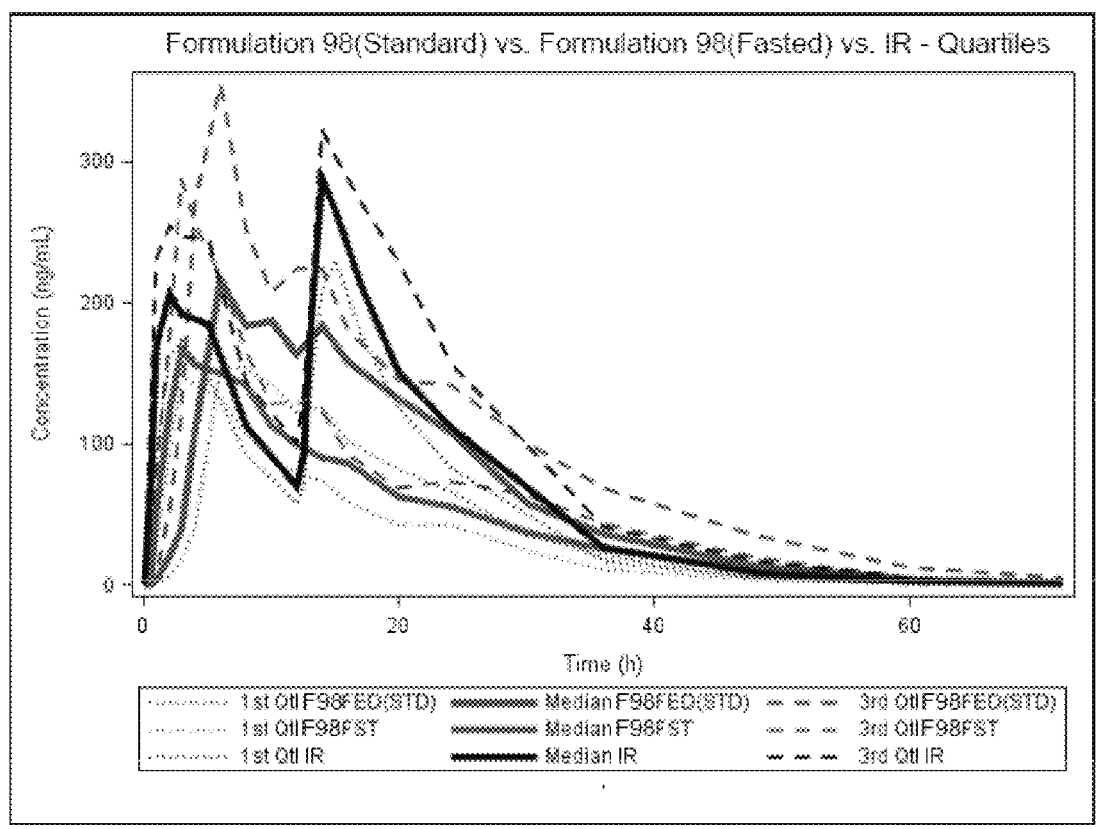
FIG. 22 shows the pharmacokinetic profile of Formulation 98 as compared to IR formulation following multiple oral doses under fasting and high fat meal conditions.
Figure 23:
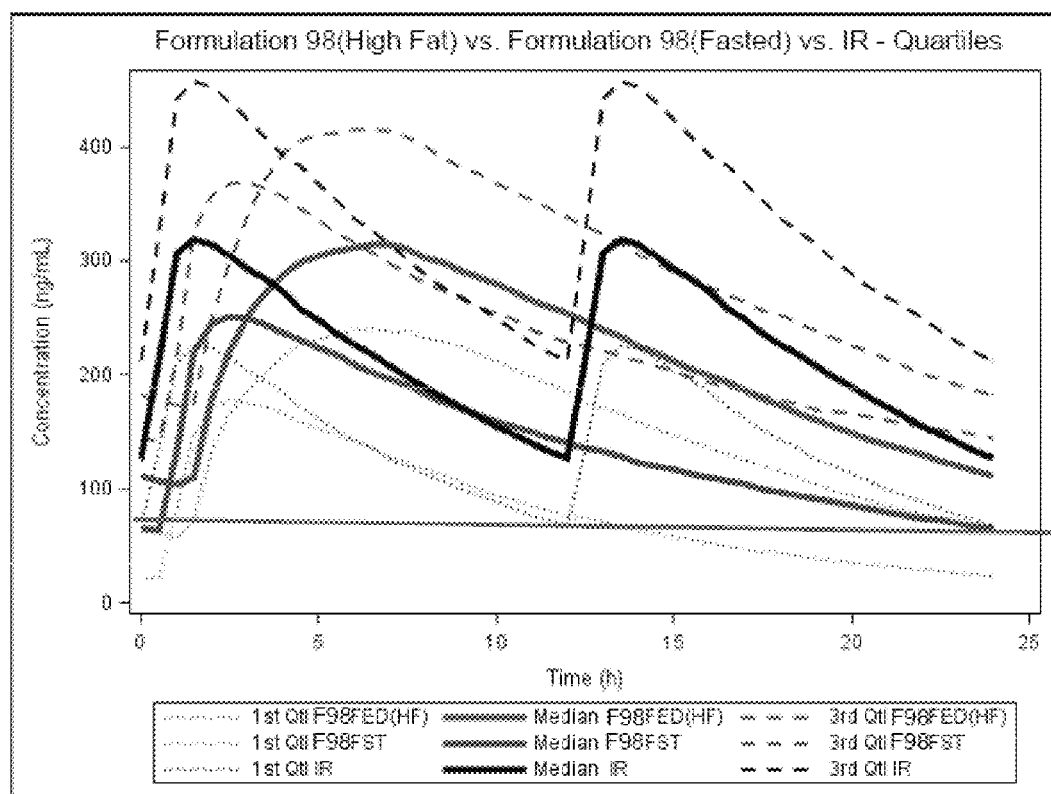
FIG. 23 shows the pharmacokinetic profile of Formulation 98 as compared to IR formulation following a single oral dose under fasting and standard meal conditions.
Figure 24:
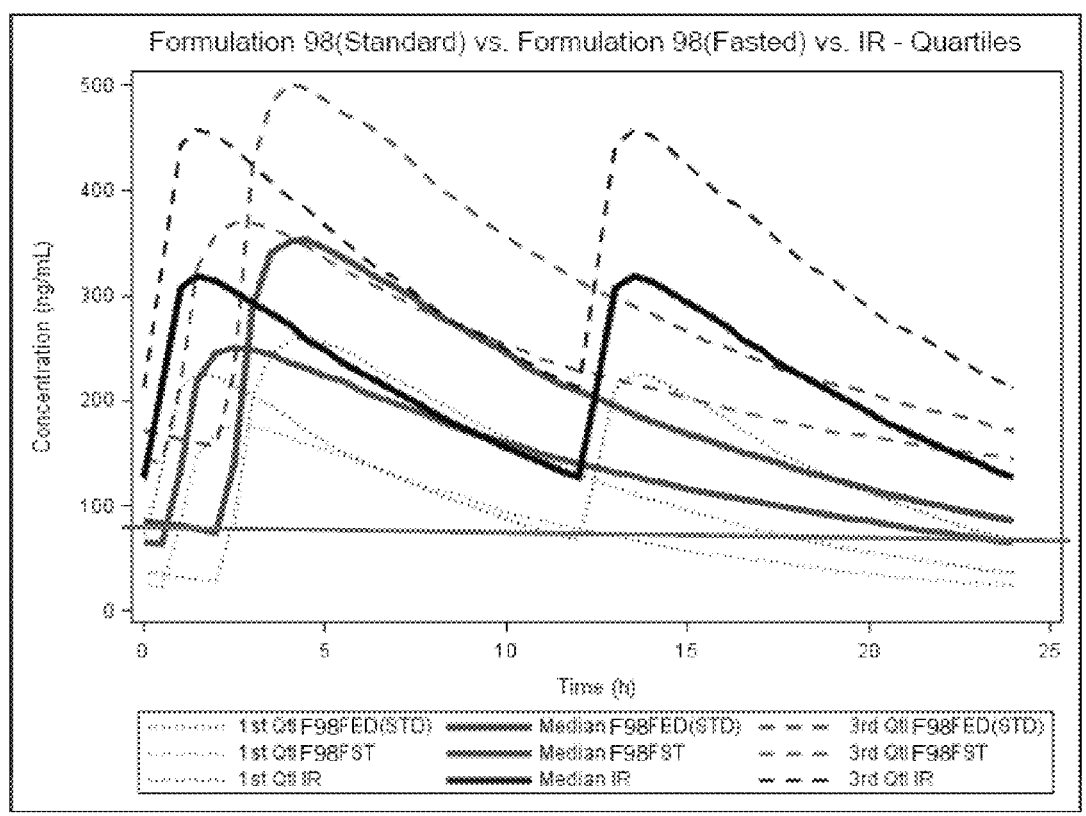
FIG. 24 shows the pharmacokinetic profile of Formulation 98 as compared to IR formulation following multiple oral doses under fasting and standard meal conditions.

Pharmacokinetic data from a single oral dose study was carried out by administering Formulation 98 to patients under fasting, standard (approximately 450 calories, 13 grams of fat), and high fat (approximately 1000 calories, 55 grams of fat) meal conditions. Plasma concentrations of Compound A in patients administered Formulation 98 are presented in FIGS. 21 and 22. Simulated steady-state plasma concentration following multiple doses are presented in FIGS. 23 and 24. Additional single dose pharmacokinetic parameters for Formulation 98 compared to an instant release formulation administered twice daily is provided in Table 6 below. The data indicates that once-daily Formulation 98 has similar pharmacokinetics to the twice-daily Instant Release Formulation. Additionally, the data shows the effect dosing under fasting and fed (high fat meal) conditions on the pharmacokinetics of Compound A. The analysis suggests that the effect of skipping a meal and/or dosing with a high fat meal on the pharmacokinetics of apremilast is expected to be minimal. As Formulation 98 is administered once daily, this convenient formulation will likely result in increased patient compliance and adherence to therapy while equivalent or better efficacy as compared to the instant release formulation.

Based on the observation during dissolution, the dosage form starts to float at about 0.5-1 hour. It remains as gel form for up to 4 hours. In contrast, the IR formulation disintegrates within 5 minutes.

TABLE 6

| Single Dose Pharmacokinetic Data Under Standard Meal Conditions Compared to Instant Release Formulation administered twice daily | | |
| --- | --- | --- |
| | Formulation #98 | Instant Release Formulation |
| Dose of Compound A | 75 mg QD | 30 mg BID |
| AUC | 4955.03 | 5184.8 |
| $C_{max}$ | 337.43 | 320.3 |

Example 13

Controlled Release Formulation

The controlled release formulation, Formulation 101, was prepared according to the methods described in U.S. Pat. No. 8,263,128.

Pharmacokinetic Profile of Formulation 101

Figure 27:
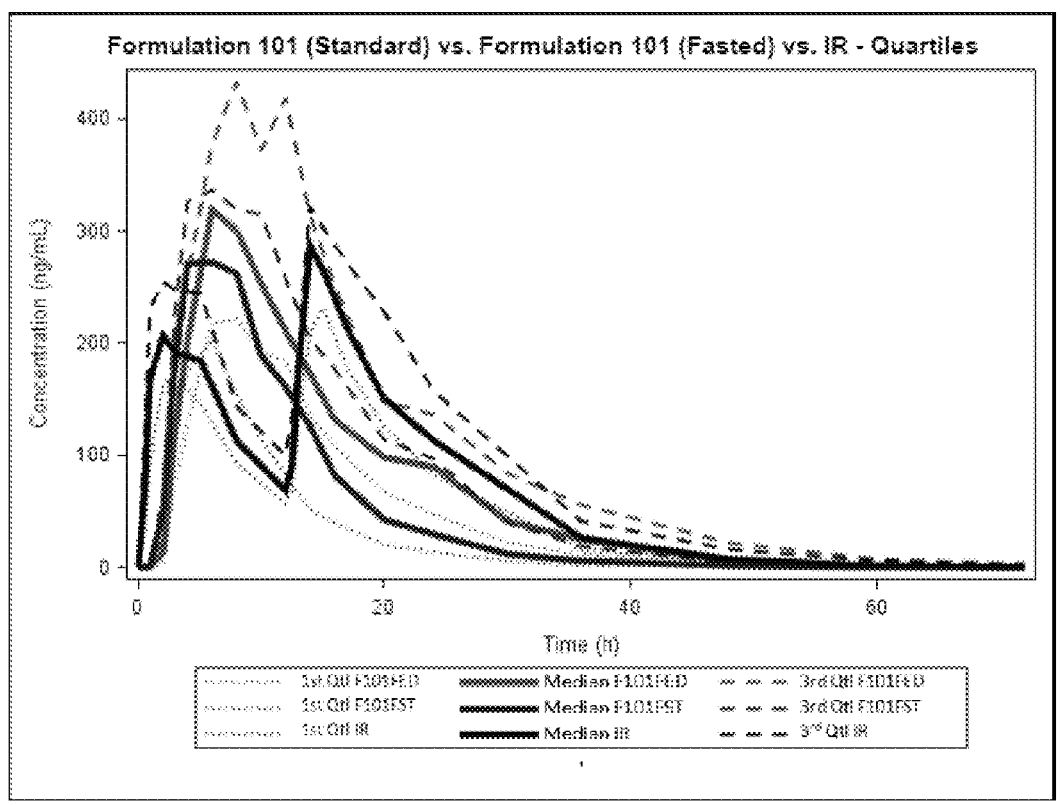
FIG. 27 shows the pharmacokinetic profile of Formulation 101 as compared to IR formulation following a single oral dose under fasting and standard meal conditions.
Figure 28:
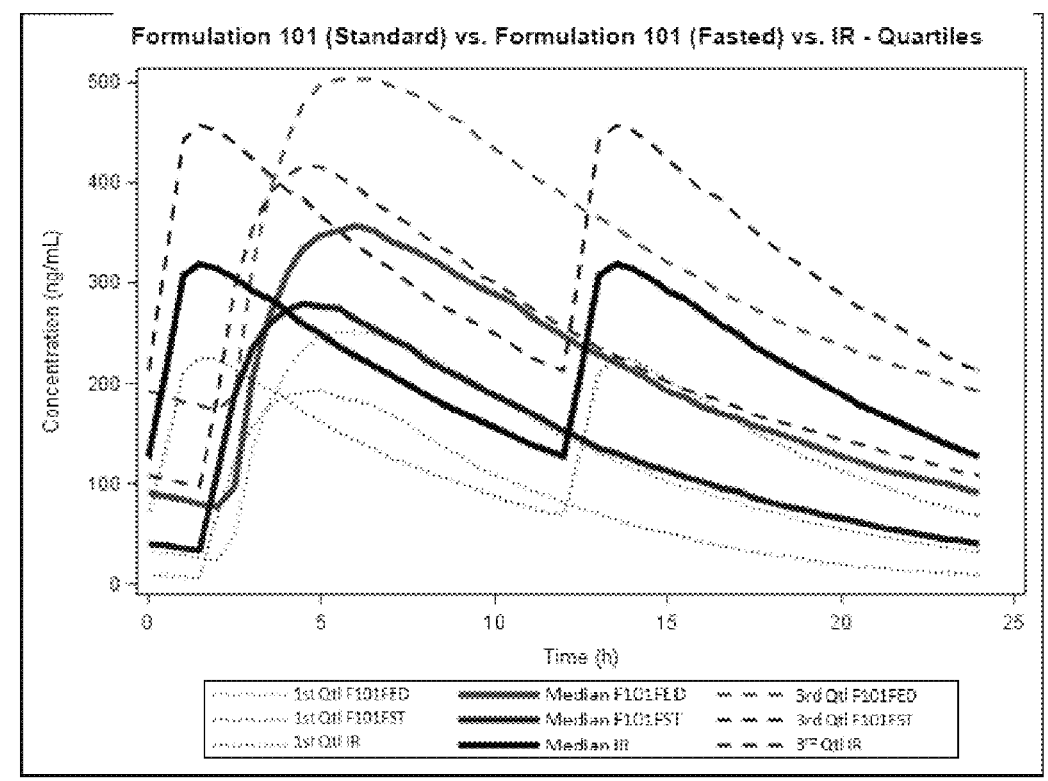
FIG. 28 shows the pharmacokinetic profile of Formulation 101 as compared to IR formulation following multiple oral doses under fasting and standard meal conditions.

Pharmacokinetic data from a single oral dose study was carried out by administering swellable core technology Formulation 101 to patients under fasting and standard (approximately 450 calories, 13 grams of fat) meal conditions. Plasma concentrations of Compound A in patients administered Formulation 101 are presented in FIG. 27. Simulated steady-state plasma concentration following multiple doses are presented in FIG. 28. Additional single dose pharmacokinetic parameters for Formulation 101 compared to an instant release formulation administered twice daily is provided in Table 7 below. The data indicates that Formulation 101 has similar pharmacokinetics to the Instant Release Formulation.

TABLE 7

Single Dose Pharmacokinetic Data Under Standard Meal Conditions Compared to Instant Release Formulation administered twice daily

|  | Formulation #101 | Instant Release Formulation |
| --- | --- | --- |
| Dose of Compound A | 75 mg QD | 30 mg BID |
| AUC | 4984.6 | 5184.8 |
| $C_{max}$ | 348.88 | 320.3 |

Example 14

Comparative Pharmacokinetic Data for Formulations 98 and 101

Comparative pharmacokinetic data from a single oral dose study was carried out by administering Formulation 98 and Formulation 101 to patients under standard (approximately 450 calories, 13 grams of fat) meal conditions. Formulation 98 contains crystalline Compound A, while Formulation 101 uses amorphous Compound A. The amorphous form of Compound A has a greater aqueous solubility as compared to crystalline forms.

Figure 29:
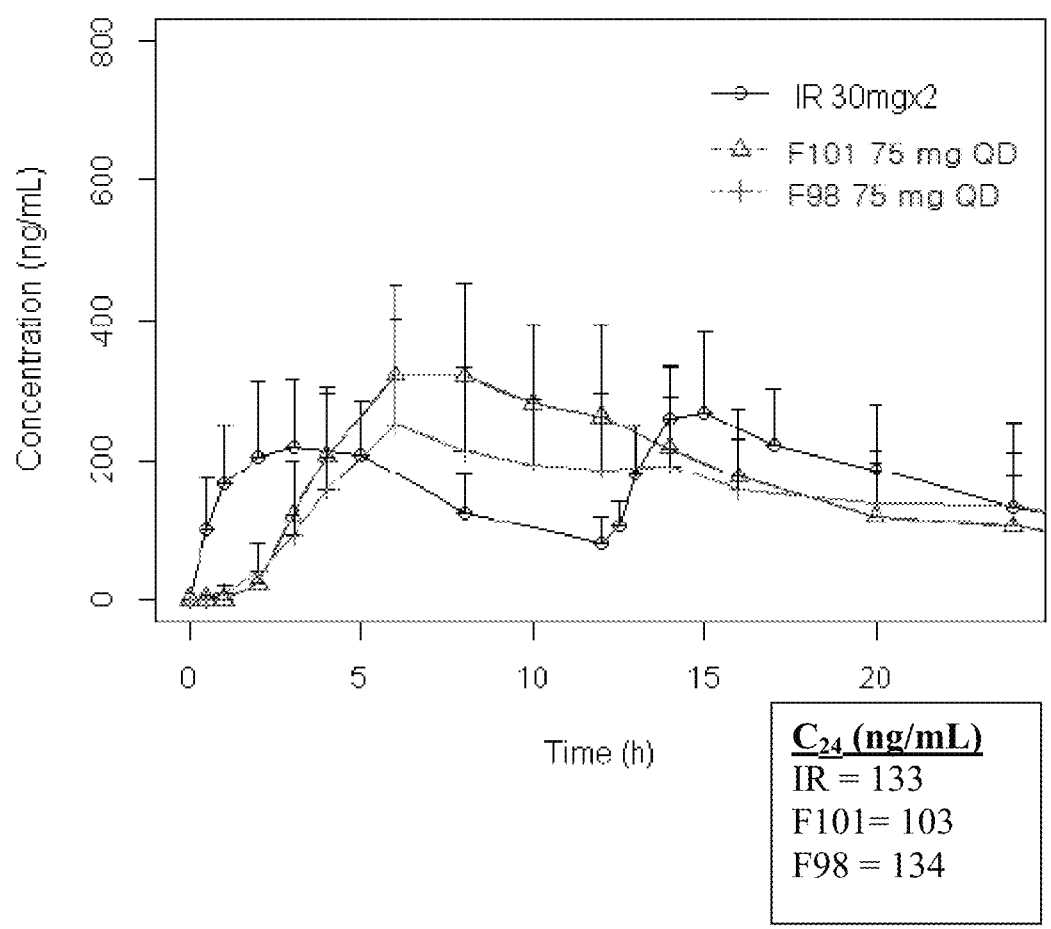
FIG. 29 shows mean plasma Apremilast profiles for single dose of Formulation 98 and Formulation 101 under standard meal conditions.

Plasma concentrations of Compound A in patients administered these formulations are presented in FIG. 29. FIG. 29 shows the once daily administration of either Formulation 98 or Formulation 101 results in similar plasma concentration of Compound A as compared to the twice-daily administration of the instant release formulation.

After 24 hours, a single dose of Formulation 98 provides a nearly identical plasma concentration of Compound A as the reference twice-daily instant release formulation, while Formulation 101 provides a plasma concentration that is about 77% of that provided by the reference twice-daily instant release formulation, as provided in Table 8 below.

TABLE 8

Concentration at 24 hours after first administration.

| Formulation | Concentration at 24 hours (ng/mL) |
| --- | --- |
| Instant Release (Reference) | 133 |
| Formulation 98 | 134 |
| Formulation 101 | 103 |

The similar $C_{24}$ value for Formulation 98 when compared to the instant release formulation make the once-daily formulation an ideal choice as a bioequivalent dosage form to the instant release formulation.

Figure 30:
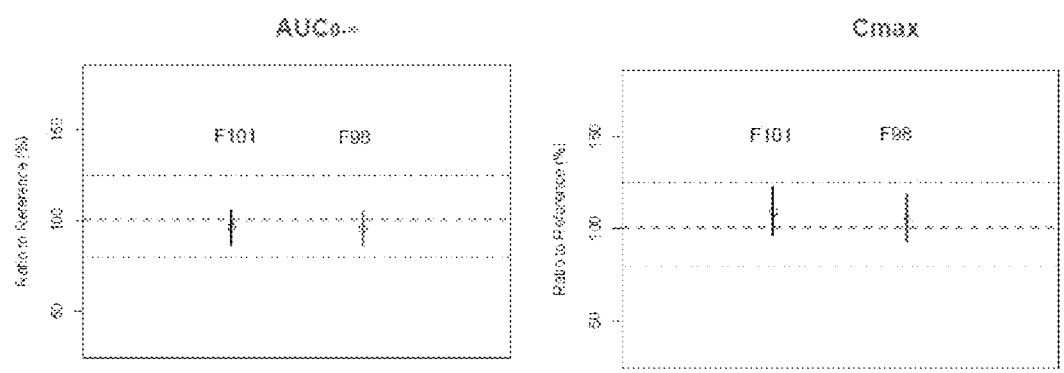
FIG. 30 shows single dose cross over study data of Formulation 98 and Formulation 101 under fed conditions to determine bioequivalence criteria.

Additional pharmacokinetic data is provided in Table 9 below. The mean and confidence interval of both Formulation 98 and Formulation 101 in the fed state fall with 80-125% bioequivalence requirement of the reference 30 mg instant release dosage taken twice daily, as shown in FIG. 30. Accordingly, both single doses of Formulation 98 and Formulation 101 are bioequivalent to the Instant Release formulation taken twice daily under fed conditions. A formulation of Compound A taken once daily will increase convenience and adherence to therapy for patients, which will allow patients to realize the full therapeutic benefit of Compound A.

TABLE 9

Single Dose Pharmacokinetic Data Under Standard Meal Conditions Compared to Instant Release Formulation administered twice daily

| Parameter (unit) | Treatment | N | Geometric Mean | Comparison | Ratio (%) of Geometric Means | 90% Confidence Interval ratio of Geometric Means | Intra-subject CV % |
| --- | --- | --- | --- | --- | --- | --- | --- |
| $AUC_{0-t}$ (h*ng/mL) | IR | 18 | 5148 | F98 vs. IR | 95.4 | 86.7, 105.0 | 17.1 |
|  | F98 | 18 | 4911 | F101 vs. IR | 96.6 | 87.5, 106.0 |  |
|  | F101 | 18 | 4957 |  |  |  |  |
| $AUC_{0-\infty}$ (h*ng/mL) | IR | 18 | 5185 | F98 vs. IR | 95.6 | 86.9, 105.1 | 17.0 |
|  | F98 | 18 | 4955 | F101 vs. IR | 96.1 | 87.5, 105.7 |  |
|  | F101 | 18 | 4985 |  |  |  |  |
| $C_{max}$ (ng/mL) | IR | 18 | 320 | F98 vs. IR | 105.3 | 93.5, 118.7 | 21.4 |
|  | F98 | 18 | 337 | F101 vs. IR | 108.9 | 96.7, 122.7 |  |
|  | F101 | 18 | 349 |  |  |  |  |

The data demonstrates that both once-daily Formulations 98 and 101 have sustained exposure properties with nearly equivalent $C_{max}$, AUC, and $C_{min}$ to the 30 mg instant release dosage taken twice daily. However, Formulation 98 provides for a more consistent concentration of Compound A over a 24-hour period than does Formulation 101, and Formulation 98 has a closer $C_{24}$ than Formulation 101.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

Each of the U.S. patents, U.S. patent application publications, foreign patents and foreign published applications recited herein are hereby incorporated by reference in their entirety.

What is claimed is:

1. A controlled release oral dosage form comprising:
(i) a compound of formula (I):

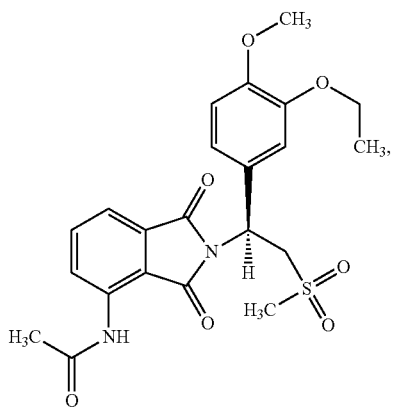

or a pharmaceutically acceptable polymorph, solvate or hydrate thereof, in an amount of about 10% by weight;
(ii) sodium carboxymethyl cellulose in an amount of about 34.5% by weight;
(iii) poly(butyl methacylate-co-2-dimethylaminoethyl methacrylate-co-methyl methacrylate) (1:2:1) in an amount of about 5% by weight;
(iv) sodium alginate in an amount of about 19% by weight;
(v) sodium bicarbonate in an amount of about 5% by weight;
(vi) citric acid in an amount of about 8% by weight;
(vii) croscarmellose sodium in an amount of about 5% by weight;
(viii) magnesium stearate in an amount of about 1.5% by weight;
(ix) mannitol in an amount of about 11.5% by weight and
(x) silicon dioxide in an amount of about 0.5% by weight.

* * * * *